US012553003B1

(12) United States Patent
Colucci et al.

(10) Patent No.: US 12,553,003 B1

(45) Date of Patent: Feb. 17, 2026

(54) QUATERNARY AMMONIUM COMPOUNDS

(71) Applicant: Afton Chemical Corporation, Richmond, VA (US)

(72) Inventors: William Jay Colucci, Glen Allen, VA (US); Paul Kondracki, Richmond, VA (US); John Loper, Henrico, VA (US); Andre Williams, Midlothian, VA (US)

(73) Assignee: Afton Chemical Corporation

( * ) Notice: Subject to any disclaimer, the term of this patent is extended or adjusted under 35 U.S.C. 154(b) by 0 days.

(21) Appl. No.: 19/044,245

(22) Filed: Feb. 3, 2025

(51) Int. Cl.
*C10L 1/224* (2006.01)
*C07C 235/74* (2006.01)

(52) U.S. Cl.
CPC ............ *C10L 1/224* (2013.01); *C07C 235/74* (2013.01); *C10L 2230/22* (2013.01)

(58) Field of Classification Search
CPC ..... C10L 1/224; C10L 2230/22; C07C 235/74
See application file for complete search history.

(56) References Cited

U.S. PATENT DOCUMENTS

| | | | |
|---|---|---|---|
| 2,129,264 | A | 9/1938 | Baxter et al. |
| 2,425,755 | A | 8/1947 | Roberts et al. |
| 2,425,845 | A | 8/1947 | Toussaint et al. |
| 2,448,664 | A | 9/1948 | Fife et al. |
| 2,457,139 | A | 12/1948 | Fife et al. |
| 2,475,755 | A | 7/1949 | Pearson |
| 2,568,876 | A | 9/1951 | White et al. |
| 2,886,423 | A | 5/1959 | Kozikowski |
| 3,015,668 | A | 1/1962 | Kozikowski |
| 3,027,246 | A | 3/1962 | Bartlett |
| 3,092,474 | A | 6/1963 | Ebner |
| 3,172,892 | A | 3/1965 | Le Suer et al. |
| 3,198,613 | A | 8/1965 | Udelhofen |
| 3,202,678 | A | 8/1965 | Stuart et al. |
| 3,216,936 | A | 11/1965 | Le Suer et al. |
| 3,219,666 | A | 11/1965 | Norman et al. |
| 3,254,025 | A | 5/1966 | Le Suer |
| 3,272,746 | A | 9/1966 | Le Suer et al. |
| 3,361,673 | A | 1/1968 | Le Suer et al. |
| 3,468,640 | A | 9/1969 | Barusch et al. |
| 3,676,089 | A | 7/1972 | Morris et al. |
| 3,778,371 | A | 12/1973 | Malec |
| 4,038,043 | A | 7/1977 | Garth |
| 4,056,531 | A | 11/1977 | Malec |
| 4,067,698 | A | 1/1978 | Steckel |
| 4,152,499 | A | 5/1979 | Boerzel et al. |

(Continued)

FOREIGN PATENT DOCUMENTS

| | | | |
|---|---|---|---|
| CA | 2089833 | A1 | 8/1993 |
| CN | 1256302 | A | 6/2000 |

(Continued)

OTHER PUBLICATIONS

European Search Report, Application No. 22190943.5, published on Jan. 26, 2023.

(Continued)

*Primary Examiner* — Cephia D Toomer
(74) *Attorney, Agent, or Firm* — Honigman LLP

(57) ABSTRACT

The present disclosure relates to novel quaternary salt compounds including, in one embodiment, a cation having a quaternary ammonium group that is coupled to a N-substituted amino ketoacetate anion as a counterion.

6 Claims, 2 Drawing Sheets

(56) References Cited

U.S. PATENT DOCUMENTS

Figure 1:
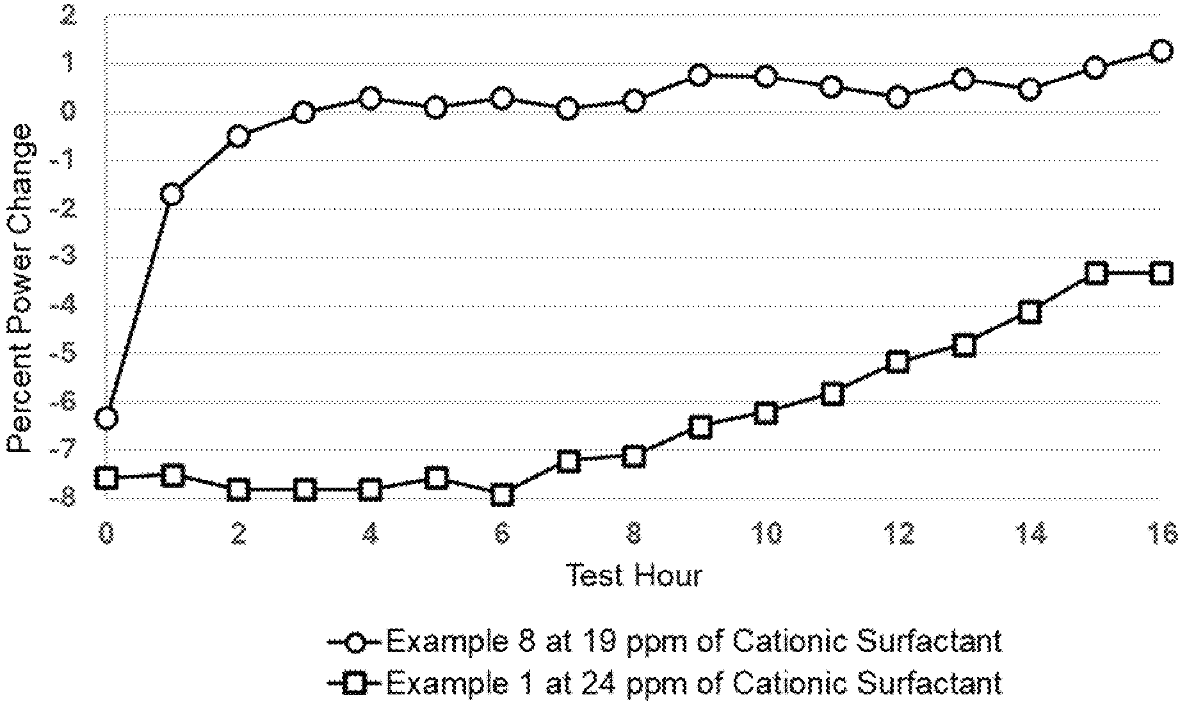

| | | | |
|---|---|---|---|
| 4,171,959 | A | 10/1979 | Vartanian |
| 4,231,759 | A | 11/1980 | Udelhofen et al. |
| 4,234,435 | A | 11/1980 | Meinhardt et al. |
| 4,248,719 | A | 2/1981 | Chafetz et al. |
| 4,253,980 | A | 3/1981 | Hammond et al. |
| 4,326,973 | A | 4/1982 | Hammond et al. |
| 4,338,206 | A | 7/1982 | Hammond et al. |
| 4,482,357 | A | 11/1984 | Hanlon |
| 4,605,808 | A | 8/1986 | Samson et al. |
| 4,613,341 | A | 9/1986 | Zaweski et al. |
| 4,729,769 | A | 3/1988 | Schlicht et al. |
| 4,787,916 | A | 11/1988 | Feldman |
| 4,844,714 | A | 7/1989 | Vogel et al. |
| 4,877,416 | A | 10/1989 | Campbell et al. |
| 5,024,677 | A | 6/1991 | Wang |
| 5,250,174 | A | 10/1993 | Hart |
| 5,254,138 | A | 10/1993 | Kurek |
| 5,330,667 | A | 7/1994 | Tiffany, III |
| 5,393,309 | A | 2/1995 | Cherpeck |
| 5,514,190 | A | 5/1996 | Cunningham et al. |
| 5,518,511 | A | 5/1996 | Russel et al. |
| 5,575,823 | A | 11/1996 | Wallace et al. |
| 5,620,486 | A | 4/1997 | Cherpeck |
| 5,634,951 | A | 6/1997 | Colucci et al. |
| 5,697,988 | A | 12/1997 | Malfer et al. |
| 5,725,612 | A | 3/1998 | Malfer et al. |
| 5,752,989 | A | 5/1998 | Henly et al. |
| 5,756,428 | A | 5/1998 | Emert et al. |
| 5,800,103 | A | 9/1998 | Malfer et al. |
| 5,814,111 | A | 9/1998 | Graham et al. |
| 5,873,917 | A | 2/1999 | Daly |
| 5,876,468 | A | 3/1999 | Moreton |
| 6,048,373 | A | 4/2000 | Malfer et al. |
| 6,166,238 | A | 12/2000 | Filipkowski et al. |
| 6,405,711 | B1 | 6/2002 | Smith et al. |
| 6,458,172 | B1 | 10/2002 | Macduff et al. |
| 6,462,014 | B1 | 10/2002 | Johnson |
| 6,475,250 | B2 | 11/2002 | Krull et al. |
| 6,548,458 | B2 | 4/2003 | Loper |
| 6,695,890 | B1 | 2/2004 | Hazel et al. |
| 6,730,773 | B2 | 5/2004 | Heinen |
| 6,800,103 | B2 | 10/2004 | Malfer et al. |
| 6,867,171 | B2 | 3/2005 | Harrison et al. |
| 7,297,675 | B2 | 11/2007 | Alef |
| 7,402,185 | B2 | 7/2008 | Aradi et al. |
| 7,435,272 | B2 | 10/2008 | Aradi et al. |
| 7,704,289 | B2 | 4/2010 | Alters et al. |
| 7,744,660 | B2 | 6/2010 | Burrington et al. |
| 7,766,982 | B2 | 8/2010 | Colucci et al. |
| 7,906,470 | B2 | 3/2011 | Stevenson et al. |
| 7,947,093 | B2 | 5/2011 | Barton et al. |
| 7,951,211 | B2 | 5/2011 | Barton et al. |
| 8,083,814 | B2 | 12/2011 | Stevenson et al. |
| 8,097,570 | B2 | 1/2012 | Boutout et al. |
| 8,153,570 | B2 | 4/2012 | Barton et al. |
| 8,231,695 | B2 | 7/2012 | Cunningham et al. |
| 8,425,627 | B2 | 4/2013 | Dietz et al. |
| 8,449,630 | B2 | 5/2013 | Lange et al. |
| 8,475,541 | B2 | 7/2013 | Fang et al. |
| 8,486,876 | B2 | 7/2013 | Brewer et al. |
| 8,496,716 | B2 | 7/2013 | Lange et al. |
| 8,529,643 | B2 | 9/2013 | Galante-Fox et al. |
| 8,557,003 | B2 | 10/2013 | Malfer et al. |
| 8,765,650 | B2 | 7/2014 | Delbridge et al. |
| 8,778,034 | B2 | 7/2014 | Cunningham |
| 8,863,700 | B2 | 10/2014 | Fang et al. |
| 8,894,726 | B2 | 11/2014 | Fang et al. |
| 8,915,977 | B2 | 12/2014 | Fang et al. |
| 8,961,623 | B2 | 2/2015 | Stevenson et al. |
| 8,974,551 | B1 | 3/2015 | Fang et al. |
| 9,017,431 | B2 | 4/2015 | Fang et al. |
| 9,062,265 | B2 | 6/2015 | Reid et al. |
| 9,340,742 | B1 | 5/2016 | Fang et al. |
| 9,951,285 | B2 | 4/2018 | Roeger-Goepfert et al. |
| 10,308,888 | B1 | 6/2019 | Schwab |
| 10,457,884 | B2 | 10/2019 | Russo et al. |
| 10,689,589 | B2 | 6/2020 | Cook |
| 10,913,910 | B2 | 2/2021 | Stevenson et al. |
| 11,884,890 | B1 | 1/2024 | Wang et al. |
| 12,024,686 | B2 | 7/2024 | Brennan et al. |
| 2003/0014910 | A1 | 1/2003 | Aradi et al. |
| 2003/0131527 | A1 | 7/2003 | Colucci et al. |
| 2004/0029766 | A1 | 2/2004 | Frick et al. |
| 2004/0060226 | A1 | 4/2004 | Bongart et al. |
| 2004/0167040 | A1 | 8/2004 | Dahlmann et al. |
| 2005/0066572 | A1 | 3/2005 | Colucci et al. |
| 2005/0120619 | A1 | 6/2005 | Koch et al. |
| 2005/0215411 | A1 | 9/2005 | Mackney et al. |
| 2006/0070293 | A1 | 4/2006 | Lange et al. |
| 2006/0168876 | A1 | 8/2006 | Colucci et al. |
| 2006/0196110 | A1 | 9/2006 | Schwahn et al. |
| 2006/0196111 | A1 | 9/2006 | Colucci et al. |
| 2006/0272597 | A1 | 12/2006 | Burrington et al. |
| 2007/0015681 | A1 | 1/2007 | Allef et al. |
| 2007/0169408 | A1 | 7/2007 | Hou et al. |
| 2007/0193119 | A1 | 8/2007 | Hoffman |
| 2007/0245621 | A1 | 10/2007 | Malfter et al. |
| 2008/0086936 | A1 | 4/2008 | Cunningham et al. |
| 2008/0113890 | A1 | 5/2008 | Moreton et al. |
| 2008/0274924 | A1 | 11/2008 | Lange et al. |
| 2008/0307698 | A1 | 12/2008 | Barton et al. |
| 2009/0049740 | A1 | 2/2009 | Hurst |
| 2009/0071065 | A1 | 3/2009 | Malfer et al. |
| 2009/0235576 | A1 | 9/2009 | Volkel et al. |
| 2009/0282731 | A1 | 11/2009 | Malfer et al. |
| 2010/0005706 | A1 | 1/2010 | Burgazli et al. |
| 2010/0024289 | A1 | 2/2010 | Smith et al. |
| 2010/0037513 | A1 | 2/2010 | Petrucci et al. |
| 2010/0037514 | A1 | 2/2010 | Malfer et al. |
| 2010/0132253 | A1 | 6/2010 | Kaufman et al. |
| 2010/0151396 | A1 | 6/2010 | Papachristos et al. |
| 2010/0236510 | A1 | 9/2010 | Shea et al. |
| 2011/0162263 | A1 | 7/2011 | Vilardo et al. |
| 2011/0185626 | A1 | 8/2011 | Barton et al. |
| 2011/0237469 | A1 | 9/2011 | Khandekar et al. |
| 2011/0258917 | A1 | 10/2011 | Garcia Castro et al. |
| 2011/0302828 | A1 | 12/2011 | Fang et al. |
| 2011/0308550 | A1 | 12/2011 | Reid |
| 2011/0315107 | A1 | 12/2011 | Grabarse et al. |
| 2012/0010112 | A1 | 1/2012 | Grabarse et al. |
| 2012/0138004 | A1 | 6/2012 | Stevenson et al. |
| 2012/0291339 | A1 | 11/2012 | Martin et al. |
| 2013/0031827 | A1 | 2/2013 | Reid et al. |
| 2013/0031828 | A1 | 2/2013 | Reid et al. |
| 2013/0104826 | A1 | 5/2013 | Burgess et al. |
| 2013/0118062 | A1 | 5/2013 | Fang et al. |
| 2013/0220255 | A1 | 8/2013 | Fang |
| 2013/0227878 | A1 | 9/2013 | Wolf et al. |
| 2013/0233267 | A1 | 9/2013 | Barbour |
| 2013/0237466 | A1 | 9/2013 | Lange et al. |
| 2013/0247450 | A1 | 9/2013 | Wolf |
| 2013/0255139 | A1 | 10/2013 | Dolmazon et al. |
| 2013/0296210 | A1 | 11/2013 | Hansch et al. |
| 2013/0298948 | A1 | 11/2013 | Company et al. |
| 2013/0312318 | A1 | 11/2013 | Peretolchin et al. |
| 2013/0324665 | A1 | 12/2013 | Shaikh et al. |
| 2013/0333650 | A1 | 12/2013 | Fang et al. |
| 2014/0157655 | A1 | 6/2014 | Tort et al. |
| 2014/0157656 | A1 | 6/2014 | Reid |
| 2014/0174390 | A1 | 6/2014 | Reid et al. |
| 2014/0196678 | A1 | 7/2014 | Fang et al. |
| 2015/0033617 | A1 | 2/2015 | Arondel et al. |
| 2015/0252277 | A1 | 9/2015 | Hansch et al. |
| 2015/0252278 | A1 | 9/2015 | Bush et al. |
| 2016/0046855 | A1 | 2/2016 | Mastrangelo et al. |
| 2016/0130514 | A1 | 5/2016 | Hansch et al. |
| 2016/0152910 | A1 | 6/2016 | Reid et al. |
| 2016/0152912 | A1 | 6/2016 | Mulqueen |
| 2016/0272912 | A1 | 9/2016 | Voelkel et al. |
| 2016/0289584 | A1 | 10/2016 | Russo et al. |
| 2017/0096610 | A1 | 4/2017 | Bush et al. |
| 2017/0096611 | A1 | 4/2017 | Stevenson et al. |
| 2017/0101594 | A1 | 4/2017 | Stevenson et al. |
| 2017/0107438 | A1 | 4/2017 | Greenfield et al. |

(56) References Cited

U.S. PATENT DOCUMENTS

| | | | |
|---|---|---|---|
| 2017/0114296 | A1 | 4/2017 | Arters et al. |
| 2017/0114297 | A1 | 4/2017 | Sampler et al. |
| 2017/0121628 | A1 | 5/2017 | Moreton et al. |
| 2017/0166826 | A1 | 6/2017 | Culley et al. |
| 2017/0218291 | A1 | 8/2017 | Reid et al. |
| 2018/0066202 | A1 | 3/2018 | Gahagan et al. |
| 2018/0223203 | A1 | 8/2018 | Cook |
| 2020/0024536 | A1 | 1/2020 | Shanahan et al. |
| 2020/0277537 | A1 | 9/2020 | Mulqueen |
| 2020/0283691 | A1 | 9/2020 | Raj Mohan et al. |
| 2021/0115347 | A1 | 4/2021 | Mulqueen et al. |

FOREIGN PATENT DOCUMENTS

| | | | |
|---|---|---|---|
| CN | 101671584 | B | 3/2010 |
| CN | 111440643 | A | 7/2020 |
| CN | 118853249 | * | 10/2024 |
| EP | 0016312 | A1 | 10/1980 |
| EP | 0293192 | A1 | 11/1988 |
| EP | 1293553 | A2 | 3/2003 |
| EP | 1411105 | A2 | 4/2004 |
| EP | 1518918 | A1 | 3/2005 |
| EP | 1918355 | A1 | 5/2008 |
| EP | 2033945 | A1 | 3/2009 |
| EP | 2531580 | A1 | 12/2012 |
| EP | 2674471 | A1 | 12/2013 |
| EP | 2739707 | A1 | 6/2014 |
| EP | 2987845 | A1 | 2/2016 |
| EP | 2776691 | B1 | 10/2018 |
| EP | 3597726 | A1 | 1/2020 |
| EP | 3447111 | B1 | 7/2022 |
| GB | 842728 | A1 | 7/1960 |
| GB | 2493377 | A | 2/2013 |
| GB | 2615408 | A | 8/2023 |
| WO | 2004050806 | A2 | 6/2004 |
| WO | 2005023965 | A1 | 3/2005 |
| WO | 2010132209 | A1 | 11/2010 |
| WO | 2011095819 | A1 | 8/2011 |
| WO | 2013000738 | A2 | 1/2013 |
| WO | 2013017889 | A1 | 2/2013 |
| WO | 2013/070503 | A1 | 5/2013 |
| WO | 2013092533 | A1 | 6/2013 |
| WO | 2014/195464 | A1 | 12/2014 |
| WO | 2015011505 | A1 | 1/2015 |
| WO | 2017097686 | A1 | 6/2017 |
| WO | 2017168312 | A1 | 10/2017 |
| WO | 2019079246 | A1 | 4/2019 |
| WO | 2020058672 | A1 | 3/2020 |

OTHER PUBLICATIONS

Shanahan, Charles S. et al. "A general method for fouling injectors in gasoline direct injection vehicles and the effects for deposits on vehicle performance" SAE Int. J. Fuels Lubr. 10(3):2017, doi: 10.4271/2017-01-2298.

Extended European Search Report, Application EP 23195793.7, dated Jan. 30, 2024.

Extended European Search Report, Application EP 23195748.1, dated Jan. 29, 2024.

Smith, S. Scott et al. Measurement and Control of Fuel Injector Deposits in Direct Injection Gasoline Vehicles, SAE International; Oct. 14, 2013. doi: 10.4271/2013-01-2616.

* cited by examiner

QUATERNARY AMMONIUM COMPOUNDS

TECHNICAL FIELD

This disclosure is directed to quaternary ammonium salts, compositions including the quaternary ammonium salts, and to methods for preparing the quaternary ammonium salts.

BACKGROUND

Quaternary ammonium salt compounds can be used in many applications and commonly found, for example, in disinfectants, fabric softeners, shampoos, detergents, fuel compositions, lubricants, soaps, cleaning products, and the like to suggest but a few applications. Quaternary ammonium salt compounds, in some instances, are obtained from an acylating agent reacted with an amine compound, which is then alkylated or quaternized by a quaternizing agent. In other instances, the quaternary ammonium compounds can be made directly by reacting a suitable amine compound with a quaternizing agent. In one particular application, quaternary ammonium salt compounds may be used as a detergent in fuel compositions for gasoline or diesel engines. Given that fuels are continually being improved to enhance various properties of the fuel composition to accommodate their use in newer and/or more-advanced engines, there is a corresponding need to further develop new and improved quaternary ammonium salt compounds that provide improved performance in such fuel compositions.

SUMMARY

In one approach or embodiment, the present disclosure provides a quaternary ammonium salt comprising (i) a cation having a quaternary ammonium group and (ii) a N-substituted amino ketoacetate anion. In some aspects of this embodiment, the N-substituted amino ketoacetate anion has a molecular weight of at least about 200 (such as about 200 to about 1500, about 200 to about 1000, about 200 to about 500, or about 300 to about 400).

In other approaches or embodiments, the quaternary ammonium salt of the previous paragraph may also include other features, elements, or embodiments in any combination. These other features, elements, or embodiments may include one or more of the following: wherein the N-substituted amino ketoacetate anion has the structure of Formula I:

(Formula I)

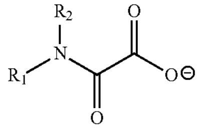

wherein $R_1$ is hydrogen, or selected from an alkyl group, an alkenyl group, an alkyl-ether group, an aryl-alkyl group, an alkyl-aryl group, an alkyl-aryl-ether group, an alkyl-polyether-alkyl group, or an aryl-polyether-alkyl group; and $R_2$ is selected from an alkyl group, an alkenyl group, an alkyl-ether group, an aryl-alkyl group, an alkyl-aryl group, an alkyl-aryl-ether group, an alkyl-polyether-alkyl group, or an aryl-polyether-alkyl group; and/or wherein any alkyl and/or alkenyl moiety thereof is at least 4 carbon atoms (or at least 6 carbons, at least 8 carbons, or at least 10 carbons and/or in other approaches, 4 to 30 carbons, 6 to 26 carbons, 8 to 20 carbons, or 10 to 18 carbons); and/or wherein the N-substituted amino ketoacetate anion is derived from dialkyl oxalate or a monoalkyl oxalate anion reacted with an amine or polyamine having a primary or secondary amine; and/or wherein the amine or polyamine having a primary or secondary amine has the structure of Formula II (Formula II)

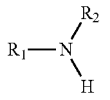

wherein each of $R_1$ and $R_2$ are, independently, a hydrogen atom, or selected from an alkyl group, an alkyl-ether group, an aryl-alkyl group, an alkyl-aryl-ether group, an alkyl-polyether-alkyl group, or an aryl-polyether-alkyl group and, in some approaches, wherein any alkyl and/or alkenyl moiety thereof is at least 3 carbon atoms, at least 4 carbon atoms, at least 6 carbons, at least 8 carbons, or at least 10 carbons (and in other approaches, may be 4 to 30 carbons, 6 to 26 carbons, 8 to 20 carbons, or 10 to 18 carbons); and/or wherein the cation having the quaternary ammonium group is a hydrocarbyl-substituted succinimide, a hydrocarbyl-substituted succinic ester, a hydrocarbyl-substituted succinic ester amide, a hydrocarbyl-substituted amide, a hydrocarbyl-substituted ester amide, Mannich reaction product, or combinations thereof; and/or wherein the cation having the quaternary ammonium group is derived from a polycarboxylic acid or anhydride reacted with an amine compound to form an intermediate reaction product including a quaternizable hydrocarbyl-substituted polycarboxylic acid or anhydride compound, wherein the amine compound includes at least one oxygen or nitrogen group capable of reacting with the polycarboxylic acid or anhydride and at least one quaternizable ammonium group; and wherein the intermediate reaction product is further reacted with a quaternizing agent that converts the at least one quaternizable amino group to a quaternary ammonium group to form the quaternary ammonium salt fuel additive; and/or wherein the amine compound has the structure of Formula VIII:

$$(R_{15})(H)N—(CH_2)_a—X_m—(CH_2)_b—X_n—(CH_2)_c—N(R_{16})(R_{17}) \quad \text{(Formula VIII)}$$

wherein each X is a bivalent moiety selected from —O—, —N(R)—, —C(O)—, —C(O)O—, or —C(O)N(R)—; $R_{15}$ is hydrogen or a hydrocarbyl group; $R_{16}$ and $R_{17}$ are, independently, a hydrocarbyl group; each R if present is, independently, a hydrogen atom or a group selected from $C_{1-6}$ aliphatic, phenyl, or alkylphenyl; m and n are, independently, integers of 0 or 1; and a, b, and c are each, independently, an integer of 1 to 10; and/or wherein both m and n are each 0 and a, b, and c are each 1; and/or wherein m is 1 and n is 0, X is —O—, and a is 3, b is 1, and c is 1; and/or wherein the amine compound has the structure of Formula IX $$R_{18}[OCH_2CHR]_n[OCHRCH_2]_mNR_{19}R_{19} \quad \text{(Formula IX)}$$

wherein each R if present is, independently, a hydrogen atom or a group selected from $C_{1-6}$ aliphatic, phenyl, or alkylphenyl; $R_{18}$ is a hydrocarbyl group, n is an integer of 1 to 20, m is an integer of 1 to 20, and each $R_{19}$ is, independently, hydrogen or a hydrocarbyl group; and/or wherein the amine compound is selected from dimethylaminoethoxy propylamine, dimethyldipropylenetriamine, dimethylamino propylamine, etheramine or polyetheramine, fatty amine or fatty polyamine, polyalkylene amine, or combinations thereof.

In yet another approach or embodiment, the present disclosure also provides a fuel composition including a major amount of a fuel (e.g., gasoline or diesel) and a minor amount of any embodiment of the quaternary ammonium salt as describes in this Summary. In one aspect, the fuel composition includes a major amount of a fuel (e.g., diesel or gasoline) and a minor amount of a fuel additive including a quaternary ammonium salt including (i) a cation having a quaternary ammonium group and (ii) a N-substituted amino ketoacetate anion. In another aspect, the N-substituted amino ketoacetate anion has a molecular weight of at least about 200 (or about 200 to about 1500, about 200 to about 1000, or about 200 to about 500, or about 300 to about 400).

In yet other approaches or embodiments, the fuel composition of the previous paragraph may include one or more other features, elements, or embodiments in any combination. These other features, elements, or embodiments may include one or more of the following: wherein the N-substituted amino ketoacetate anion has the structure of Formula I:

(Formula I)

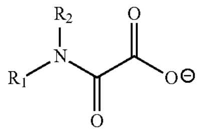

wherein $R_1$ is hydrogen, or selected from an alkyl group, an alkenyl group, an alkyl-ether group, an aryl-alkyl group, an alkyl-aryl group, an alkyl-aryl-ether group, an alkyl-polyether-alkyl group, or an aryl-polyether-alkyl group; and $R_2$ is hydrogen, or selected from an alkyl group, an alkenyl group, an alkyl-ether group, an aryl-alkyl group, an alkyl-aryl group, an alkyl-aryl-ether group, an alkyl-polyether-alkyl group, or an aryl-polyether-alkyl group; and/or wherein any alkyl and/or alkenyl moiety thereof is at least 4 carbon atoms (or at least 6 carbons, at least 8 carbons, or at least 10 carbons (and in other approaches, may be 4 to 30 carbons, 6 to 26 carbons, 8 to 20 carbons, or 10 to 18 carbons)); and/or wherein the N-substituted amino ketoacetate anion is derived from dialkyl oxalate or a monoalkyl oxalate anion reacted with an amine or polyamine having a primary or secondary amine; and/or wherein the amine or polyamine having a primary or secondary amine has the structure of Formula II (Formula II)

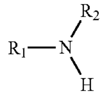

wherein each of $R_1$ and $R_2$ are, independently, a hydrogen atom, or selected from an alkyl group, an alkyl-ether group, an aryl-alkyl group, an alkyl-aryl-ether group, an alkyl-polyether-alkyl group, or an aryl-polyether-alkyl group; and/or wherein any alkyl and/or alkenyl moiety thereof is at least 3 carbon atoms (or at least about 4 carbon atoms, at least 6 carbons, at least 8 carbons, or at least 10 carbons (and in other approaches, may be 4 to 30 carbons, 6 to 26 carbons, 8 to 20 carbons, or 10 to 18 carbons)); and/or wherein the cation having the quaternary ammonium group is a hydrocarbyl-substituted succinimide, a hydrocarbyl-substituted succinic ester, a hydrocarbyl-substituted succinic ester amide, a hydrocarbyl-substituted amide, a hydrocarbyl-substituted ester amide, Mannich reaction product, or combinations thereof; and/or wherein the cation having the quaternary ammonium group is derived from a polycarboxylic acid or anhydride reacted with an amine compound to form an intermediate reaction product including a quaternizable hydrocarbyl-substituted polycarboxylic acid or anhydride compound, wherein the amine compound includes at least one oxygen or nitrogen group capable of reacting with the polycarboxylic acid or anhydride and at least one quaternizable ammonium group; and (ii) wherein the intermediate reaction product is further reacted with a quaternizing agent that converts the at least one quaternizable amino group to a quaternary ammonium group to form the quaternary ammonium salt fuel additive; and/or wherein the amine compound has the structure of Formula VIII:

$(R_{15})(H)N—(CH_2)_a—X_m—(CH_2)_b—X_n—(CH_2)_c—N(R_{16})(R_{17})$ (Formula VIII)

wherein each X is a bivalent moiety selected from —O—, —N(R)—, —C(O)—, —C(O)O—, or —C(O)N(R)—; $R_{15}$ is hydrogen or a hydrocarbyl group; $R_{16}$ and $R_{17}$ are, independently, a hydrocarbyl group; each R if present is, independently, a hydrogen atom or a group selected from $C_{1-6}$ aliphatic, phenyl, or alkylphenyl; m and n are, independently, integers of 0 or 1; and a, b, and c are each, independently, an integer of 1 to 10; and/or wherein both m and n are each 0 and a, b, and c are each 1; and/or wherein m is 1 and n is 0, X is —O—, and a is 3, b is 1, and c is 1; and/or wherein the amine compound has the structure of Formula IX $R_{18}[OCH_2CHR]_n[OCHRCH_2]_mNR_{19}R_{19}$ (Formula IX)

wherein each R if present is, independently, a hydrogen atom or a group selected from $C_{1-6}$ aliphatic, phenyl, or alkylphenyl; $R_{18}$ is a hydrocarbyl group, n is an integer of 1 to 20, m is an integer of 1 to 20, and each $R_{19}$ is, independently, hydrogen or a hydrocarbyl group; and/or wherein the amine compound is selected from dimethylaminoethoxy propylamine, dimethyldipropylenetriamine, dimethylamino propylamine, etheramine or polyetheramine, fatty amine or fatty polyamine, polyalkylene amine, or combinations thereof, and/or wherein the quaternary ammonium salt provides about 1 to about 100 ppm of the cation and about 1 to about 100 ppm of the anion.

In yet other approaches or embodiments, any embodiment of the fuel compositions of this Summary (e.g., gasoline, diesel, etc.) may contain, on an active ingredient basis, an amount of any embodiment of the quaternary ammonium salt compound (or reaction product as described herein) of this Summary in the range of about 1 ppm to about 100 ppm, in other approaches, about 3 ppm to about 50 ppm, in yet further approaches about 5 ppm to about 45 ppm of the quaternary ammonium salt, about 5 to about 40 ppm, or about 5 to about 25 ppm of the quaternary ammonium salt. In other embodiments where the fuel is gasoline, an amount of the quaternary ammonium salt compound (or reaction product as described herein) is in the range of about 1 ppm to about 100 ppm, in other approaches, about 3 ppm to about 50 ppm, in yet further approaches about 4 ppm to about 40 ppm, or about 5 to about 20 ppm, or about 5 to about 10 ppm of the quaternary ammonium salt is used. In yet other embodiments where the fuel is diesel, an amount of the quaternary ammonium salt compound (or reaction product as described herein) is in the range of about 1 ppm to about 200 ppm, in other approaches, about 10 ppm to about 100 ppm, in yet further approaches about 20 ppm to about 60 ppm of the quaternary ammonium salt, in yet further approaches about 30 ppm to 50 ppm of the quaternary ammonium salt is used.

In yet other embodiments, any embodiment of the quaternary ammonium salt compounds of this Summary may provide to a fuel composition about 1 to about 100 ppm of a cation (in other approaches where the fuel is gasoline, about 3 ppm to about 50 ppm of a cation, or about 5 ppm to about 30 ppm of a cation, or about 5 to about 25 ppm of a cation, or about 5 to about 20 ppm of a cation; and in other approaches where the fuel is diesel, about 5 ppm to about 80 ppm of a cation, or about 10 ppm to about 50 ppm of a cation, or about 10 to about 45 ppm of a cation, or about 20 to about 40 ppm of a cation) and about 1 ppm to about 100 ppm of an anion (in other approaches where the fuel is gasoline, about 3 ppm to about 30 ppm of an anion, or about 5 ppm to about 25 ppm of an anion, or about 5 to about 16 ppm of an anion; and in other approaches where the fuel is diesel, about 5 ppm to about 80 ppm of an anion, or about 10 ppm to about 50 ppm of an anion, or about 10 to about 25 ppm of an anion. The anion or the cation is any embodiment as described in this Summary.

In yet other embodiments, the use of any embodiment of the quaternary ammonium salt and/or fuel composition of this Summary is described for reducing injector deposits in an internal combustion system or engine or within a fuel system for an internal combustion system or engine, cleaning-up fouled injectors, and/or un-sticking injectors (e.g., as measured via the DW-10B diesel engine test, CEC F-98-08 or other clean-up evaluation as described herein). The internal combustion engine can be either a diesel engine or gasoline engine.

DESCRIPTION OF DRAWING FIGURES

Figure 2:
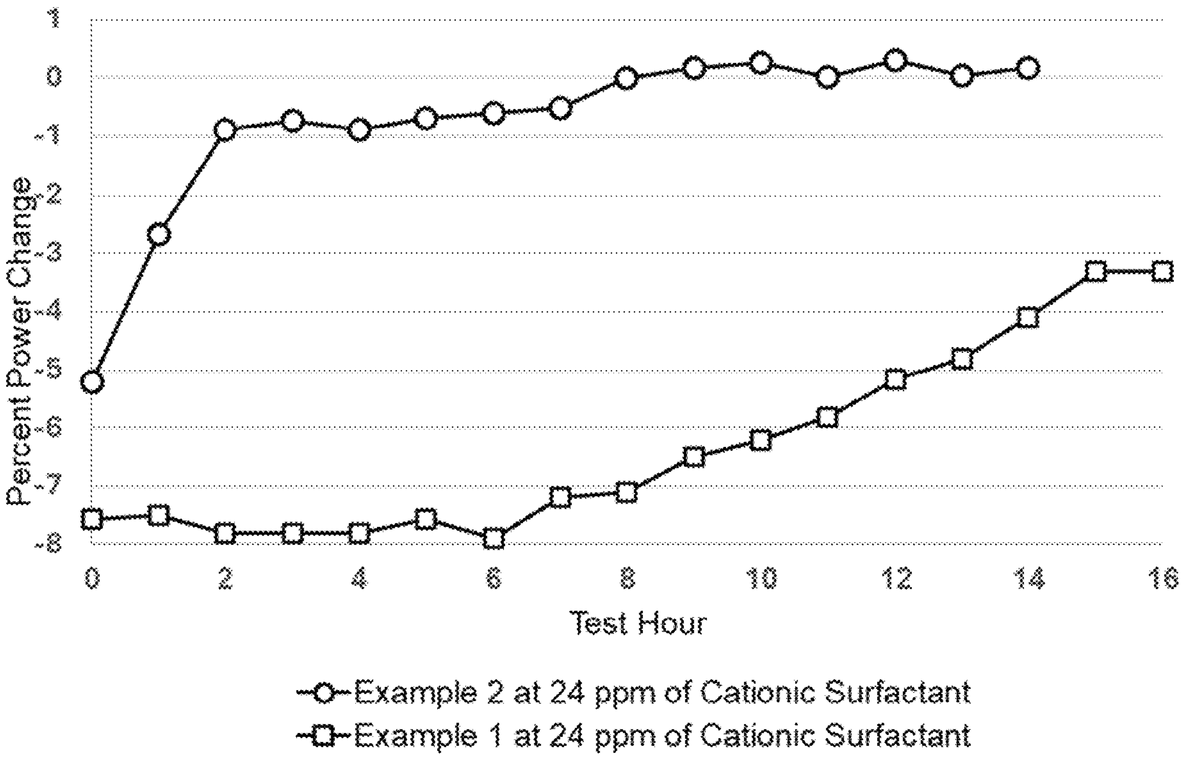

FIG. 1 is a plot of DW10B power recovery of Quaternary Ammonium Salts from Example 1 (Comparative) and Example 8 (Inventive); and FIG. 2 is a plot of DW10B power recovery of Quaternary Ammonium Salts from Example 1 (Comparative) and Example 2 (Inventive).

DETAILED DESCRIPTION

Quaternary ammonium compounds are organic compounds including a positively charged nitrogen atom bonded to four organic groups forming a cationic compound. In one approach, quaternary ammonium compounds can be coupled cationic and anionic compounds or salt systems including a positively charged cation having a quaternary ammonium group (e.g., a nitrogen atom bonded to four organic groups) and a negatively charged anion as a counterion. In one circumstance, quaternary ammonium salt compounds may be formed by first reacting a hydrocarbyl-substituted polycarboxylic acid or anhydride with an amine compound to form an intermediate reaction product including a quaternizable hydrocarbyl-substituted polycarboxylic acid or anhydride compound. Exemplary amine compounds may include at least one oxygen or nitrogen group capable of reacting with the polycarboxylic acid or anhydride and the amine compounds may further include at least one quaternizable amino group. Next, this intermediate reaction product is further reacted with a quaternizing or alkylating agent that converts the at least one quaternizable amino group to a quaternary amino group to form the quaternary ammonium salt compound.

The present disclosure relates to quaternary salt compounds including, in one embodiment, a cation having a quaternary ammonium group that is coupled to a novel N-substituted amino ketoacetate anion as a counterion. Preferably, the quaternary ammonium salt compounds of the present disclosure include the N-substituted amino ketoacetate anion having a molecular weight of at least about 200, which aids in performance, in some circumstances, when such compounds are used as a detergent in gasoline or diesel fuel compositions. In such implementations, the N-substituted amino ketoacetate anion has a relatively long organic chain that helps keep the compound soluble in the fuel compositions.

Quaternary Ammonium Salt Anion

As noted above, the novel anionic counterion of the quaternary ammonium salt compounds herein is a N-substituted amino ketoacetate anion that preferably has a molecular weight of at least about 200 (such as a molecular weight of about 200 to about 1500, about 200 to about 1000, about 200 to about 500, or about 300 to about 400). In one approach or embodiment, the N-substituted amino ketoacetate anion has the structure of Formula I.

(Formula I)

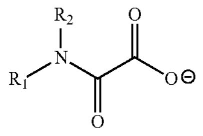

wherein $R_1$ is hydrogen, or selected from an alkyl group, an alkenyl group, an alkyl-ether group, an aryl-alkyl group, an alkyl-aryl group, an alkyl-aryl-ether group, an alkyl-polyether-alkyl group, or an aryl-polyether-alkyl group; and $R_2$ is selected from an alkyl group, an alkenyl group, an alkyl-ether group, an aryl-alkyl group, an alkyl-aryl group, an alkyl-aryl-ether group, an alkyl-polyether-alkyl group, or an aryl-polyether-alkyl group. $R_1$ and $R_2$ are preferably selected to achieve the noted minimum molecular weights and, in some approaches, any alkyl and/or alkenyl moiety of $R_1$ and/or $R_2$ noted above is at least 4 carbons, at least 6 carbons, at least 8 carbons, or at least 10 carbons (and in other approaches, may be 4 to 30 carbons, 6 to 26 carbons, 8 to 20 carbons, or 10 to 18 carbons).

In one approach or embodiment, the N-substituted amino ketoacetate anion is derived from a dialkyl oxalate (preferably dimethyl oxalate) reacted with an amine or polyamine having a primary or secondary nitrogen, which is then used as a quaternizing or alkylating agent to form the quaternary ammonium group and associated anionic counterion (e.g., shown below in exemplary Reaction Scheme A). In another approach or embodiment, the N-substituted amino ketoacetate anion is derived from a monoalkyl oxalate anion alkylating agent (preferably a monomethyl oxalate anion) that is subsequently reacted with an amine or polyamine with a primary or secondary nitrogen (e.g., shown below in exemplary Reaction Scheme B).

Exemplary Reaction Scheme A:

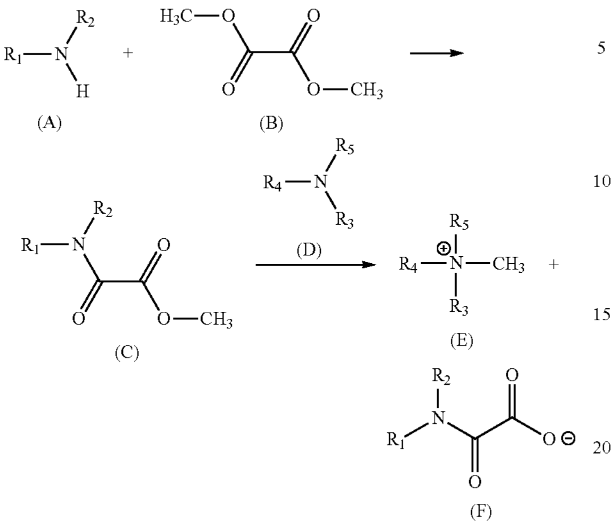

where exemplary Reaction Scheme A includes the following compounds and/or reactants: (A) is an amine compound with a primary or secondary nitrogen, (B) is a dialkyl oxalate (preferably dimethyl oxalate as depicted above), (C) is an example of a novel alkylating or methylating agent being the reaction product of (A) and (B), (D) is a compound having tertiary amino group, and (E) and (F) are the formed quaternary ammonium salt compound of the present disclosure (e.g., a coupled anionic and cationic compound or surfactant) including (E) that is a cation with a quaternary ammonium group and (F) that is the novel N-substituted amino ketoacetate anion as the counterion in the formed quaternary ammonium salt.

Exemplary Reaction Scheme B:

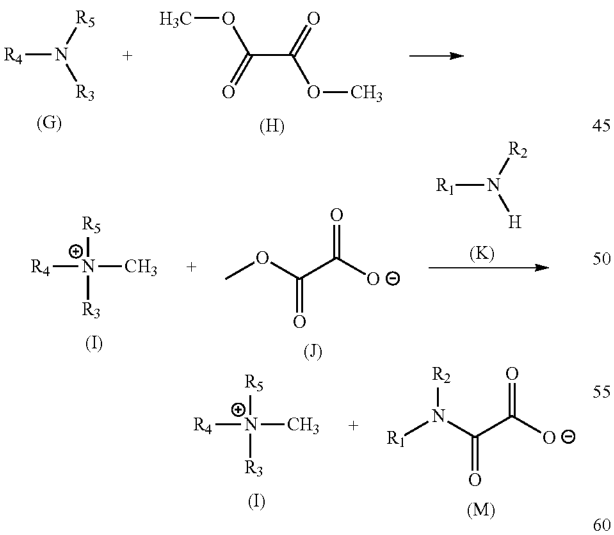

where exemplary Reaction Scheme B includes the following compounds or reactants: (G) is a compound having a tertiary amino group, (H) is a dialkyl oxalate (preferably dimethyl oxalate as depicted above), (I) and (J) represent an intermediate quaternary ammonium salt compound being the reaction product of (G) and (H) and include (I) a cation with a quaternary ammonium group and (J) an intermediate anionic counterion (e.g. monomethyl oxalate as depicted above), (K) is an amine compound having a primary or secondary nitrogen suitable to form the novel anions of the present disclosure, and (I) and (M) are the formed quaternary ammonium salt compound of the present disclosure (e.g., a coupled anionic and cationic compound or surfactant) including (I) a cation with a quaternary ammonium group and (M) the novel N-substituted amino ketoacetate anion as the counterion in the formed quaternary ammonium salt.

Exemplary Reaction Scheme C:

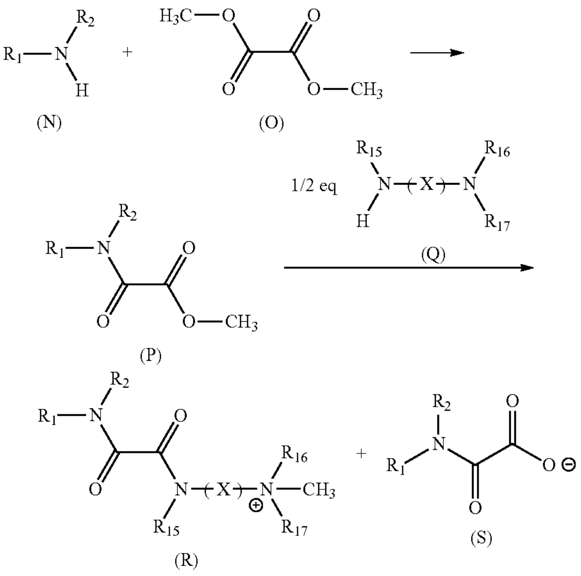

The above scheme C illustrates a "one-pot" reaction to prepare the quaternary ammonium salt of this application. Primary or secondary amine compound (N) reacts with DMO (O) to form N-substituted amino ketoacetate monoester (P). This monoester is treated with ½ molar equivalent of diamine (Q) which contains a tertiary amino group and a primary or secondary amino group (or hydroxy group). The primary and secondary amino group of (Q) reacts with the ester of a half equivalent of (P) to form a di-amide compound containing a tertiary amino group, which subsequently reacts with the remaining second half equivalent of (P) to form a quaternary ammonium salt containing the Cation (R) and Anion (S). If the diamine (Q) is replaced with an amine compound containing a hydroxy group (instead of the primary and secondary amino group), the final quaternary ammonium salt contains an ester group instead of amide group in the Cation (R), which compound is also part of this invention.

In each of the above Reaction Schemes A, B, and C, each of $R_1$ and $R_2$ of the amine compound (A), (K), and/or (N) are discussed more below and, independently, are a hydrogen atom, or selected from an alkyl group, an alkyl-ether group, an aryl-alkyl group, an alkyl-aryl-ether group, an alkyl-polyether-alkyl group, or an aryl-polyether-alkyl group. Preferably, $R_1$ and $R_2$ are selected such that the formed anion has a molecular weight of at least about 200 as noted above. Furthermore, each of $R_3$, $R_4$, and $R_5$ is selected from hydrocarbyl groups containing from 1 to 200 carbon atoms. Each hydrocarbyl group $R_3$ to $R_5$ may independently be linear, branched, substituted, cyclic, saturated, unsaturated, or contain one or more hetero atoms. Suitable hydrocarbyl groups may include, but are not limited to alkyl groups, aryl groups, alkylaryl groups, arylalkyl groups, alkoxy groups, aryloxy groups, amido groups, ester groups, imido groups, succinimide derivatives thereof, and the like. $R_{15}$, $R_{16}$, and $R_{17}$ are as described below. Any of the foregoing hydrocarbyl groups may also contain hetero atoms, such as oxygen or nitrogen atoms.

Suitable examples of the amine or polyamine with a primary or secondary nitrogen used to form the novel anionic counterions of the quaternary ammonium salt compounds via Reaction Schemes A or B above (e.g., compounds (A) or (K) in the reaction schemes) may include, but are not limited to, dimethylaminoethoxypropylamine, dimethyldipropylenetriamine, dimethylamino propylamine, etheramines or polyetheramines, fatty amines or fatty polyamines (e.g., oleyl amines), polyalkylene amines (e.g., polyisobutyleneamine), branched-chain amines (e.g., 2-ethyl hexylamine), dialkylamines or polyamines (e.g., dioctylamine, dibutylamine, tetraethylene pentaamine, triethylenetetramine, and the like), hyperbranched amines or polyamines (e.g., tetrapropenylamine, tributenylamine, and the like), oleyl propylene diamine and the like, or combinations thereof.

In yet other approaches or embodiments, the amine or polyamine having a primary or secondary amine suitable to form the novel anion counterions of the present disclosure may have the structure of Formula II (Formula II)

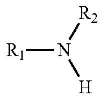

wherein each of $R_1$ and $R_2$ are, independently, a hydrogen atom, or selected from an alkyl group, an alkyl-ether group, an aryl-alkyl group, an alkyl-aryl-ether group, an alkyl-polyether-alkyl group, or an aryl-polyether-alkyl group. Preferably, $R_1$ and $R_2$ are selected such that the formed anion has a molecular weight of at least about 200 as noted above, and in this context, any alkyl and/or alkenyl moiety of Formula II is at least 3 carbon atoms or sufficient to achieve the desired molecular weight of the anion. In one embodiment, $R_1$ and $R_2$ are, independently, a hydrogen atom, or selected from a C8 to C20-alkyl group, a C8 to C20-alkyl-ether or polyether group, an aryl-C8 to C20-alkyl group, a C8 to C20-alkyl-aryl-ether or polyether group, a C8 to C20-alkyl-polyether-C8 to C20-alkyl group, or an aryl-polyether-C8 to C20-alkyl group. In yet other embodiments, suitable amine compounds having a primary or secondary amine may be described in one or more of the following: WO 2013/070503; EP 2776691; U.S. Pat. No. 9,017,431; US 2020/0277537; EP 3 447 111; U.S. Pat. No. 10,913,910; WO 2014/195464; GB 2 615 408; and/or U.S. Pat. No. 10,308,888 with relevant portions thereof incorporated herein by reference.

Quaternary Ammonium Salt Cation

The quaternary ammonium salt compounds of the present disclosure may also include a positively charged cation having a quaternary ammonium group. While the cation is not particularly limited and may include a wide variety of positively charged cations having a quaternary ammonium group, in some embodiments, exemplary cations may be derived from a hydrocarbyl-substituted succinimide, a hydrocarbyl-substituted succinic ester, a hydrocarbyl-substituted succinic ester amide, a hydrocarbyl-substituted amide, a hydrocarbyl-substituted ester amide, a Mannich reaction product, and the like, or combinations thereof. Exemplary cations for the quaternary ammonium salts of the present disclosure are described in one or more of the following WO2013/070503; EP 2 776 691; US 2020/0277537; EP 3 447 111; U.S. Pat. No. 10,913,910; WO 2014/195464; GB 2,615,408; U.S. Pat. No. 10,308,888, which are incorporated herein by reference.

Polycarboxylic Acid or Anhydride Derived Cation: In one particular approach or embodiment, the cation of the quaternary ammonium salts herein having the quaternary ammonium group is derived from (i) a polycarboxylic acid or anhydride reacted with an amine compound to form an intermediate reaction product including a quaternizable hydrocarbyl-substituted polycarboxylic acid or anhydride compound, wherein the amine compound (discussed more below) includes at least one oxygen or nitrogen group capable of reacting with the polycarboxylic acid or anhydride and further includes at least one quaternizable ammonium group; and (ii) wherein the intermediate reaction product is further reacted with a quaternizing agent (e.g. Reaction Scheme A or B above) that converts the at least one quaternizable amino group to a quaternary ammonium group to form the quaternary ammonium salt compound.

In embodiments, the hydrocarbyl substituted polycarboxylic acid or anhydride is a hydrocarbyl substituted succinic acid, ester, anhydride, mono-acid/mono-ester, or diacid. In one approach, the hydrocarbyl substituted polycarboxylic acid or anhydride may be selected from stearic acid, oleic acid, linoleic acid, linolenic acid, palmitic acid, palmitoleic acid, lauric acid, myristic acid, myristoleic acid, capric acid, caprylic acid, arachidic acid, behenic acid, erucic acid, anhydride derivatives thereof, or a combination thereof.

In one approach, the hydrocarbyl substituted polycarboxylic acid or anhydride suitable to form the cations herein may be a hydrocarbyl substituted dicarboxylic anhydride of the general formula below

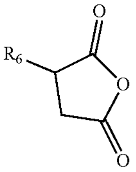

wherein $R_6$ of the structure above is a hydrocarbyl or alkenyl group. In some aspects, $R_6$ is a hydrocarbyl group having a number average molecular weight from about 200 to about 2500. For example, the number average molecular weight of $R_6$ may range from about 600 to about 1300, as measured by GPC using polystyrene as a calibration reference. A particularly useful $R_6$ has a number average molecular weight of about 1000 Daltons and comprises polyisobutylene.

In some approaches, the $R_6$ hydrocarbyl moiety of the structure in the previous paragraph may comprise one or more polymer units chosen from linear or branched alkenyl units. In some aspects, the alkenyl units may have from about 2 to about 10 carbon atoms. For example, the polyalkenyl radical may comprise one or more linear or branched polymer units formed from ethylene radicals, propylene radicals, butylene radicals, pentene radicals, hexene radicals, octene radicals and decene radicals. In some aspects, the $R_6$ polyalkenyl radical may be in the form of, for example, a homopolymer, copolymer or terpolymer. In other aspects, the polyalkenyl radical is polyisobutylene. For example, the polyalkenyl radical may be a homopolymer of polyisobutylene comprising from about 5 to about 60 isobutylene groups, such as from about 15 to about 30 isobutylene groups. The polyalkenyl compounds used to form the $R_6$ polyalkenyl radicals may be formed by any suitable methods, such as by conventional catalytic oligomerization of alkenes.

In some aspects, high reactivity polyisobutylenes having relatively high proportions of polymer molecules with a terminal vinylidene group may be used to form the above $R_6$ group. In one example, at least about 60%, such as about 70% to about 90%, of the polyisobutenes comprise terminal olefinic double bonds. In some aspects, approximately one mole of maleic anhydride may be reacted per mole of polyalkylene, such that the resulting polyalkenyl succinic anhydride has about 0.8 to about 1.5 succinic anhydride group per polyalkylene substituent. In other aspects, the molar ratio of succinic anhydride groups to polyalkylene groups may range from about 0.5 to about 3.5, such as from about 1 to about 1.3.

Mannich-Based Cation: In yet another approach or embodiment, the cation of the quaternary ammonium salts herein may be derived from a Mannich reaction product or derivative thereof having at least one tertiary amino group and derived, for example, from a hydrocarbyl-substituted phenol, cresol, or derivative thereof; an aldehyde; and an amine compound (discussed more below) having at least one quaternizable ammonium group (e.g., tertiary amino group). In this context, Mannich reaction products are first obtained from hydrocarbyl-substituted hydroxyaromatic compounds. Representative hydrocarbyl-substituted hydroxyaromatic compounds suitable for forming the cation of the Mannich-based quaternary salts herein may include those of Formula V (Formula V)

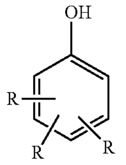

where each R of Formula V is independently hydrogen, a C1-C4 alkyl group, or a hydrocarbyl substituent having a number average molecular weight (Mn) in the range of about 300 to about 5,000 (in other approaches, about 300 to about 2,000 and particularly about 500 to about 1,500) as determined gel permeation chromatography (GPC). In some approaches, at least one R is hydrogen and one R is a hydrocarbyl substituent as defined above.

In some approaches, suitable hydrocarbyl substituents may include polyolefin polymers or copolymers, such as polypropylene, polybutene, polyisobutylene, and ethylene alpha-olefin copolymers. Examples include polymers or copolymers of butylene and/or isobutylene and/or propylene, and one or more mono-olefinic co-monomers (e.g., ethylene, 1-pentene, 1-hexene, 1-octene, 1-decene, and the like) where the copolymer may include at least 50% by weight, of butylene and/or isobutylene and/or propylene units. The co-monomers polymerized with propylene or such butenes may be aliphatic and can also contain non-aliphatic groups, e.g., styrene, o-methylstyrene, p-methylstyrene, divinyl benzene and the like. Polyolefin polymer hydrocarbyl substituents can have at least 20%, in some cases at least 50%, and in other cases at least 70% of their olefin double bonds at a terminal position on the carbon chain as the highly reactive vinylidene isomer.

Polybutylene is one useful hydrocarbyl substituent for the hydroxyaromatic compound. Polybutylene substituents may include 1-butene or isobutene, as well as polymers made from mixtures of two or all three of 1-butene, 2-butene and isobutene. Polyisobutylene is another suitable hydrocarbyl substituent for the hydroxyaromatic compounds herein. High reactivity polyisobutenes having relatively high proportions of polymer molecules with a terminal vinylidene group, such as, at least 20% of the total terminal olefinic double bonds in the polyisobutene comprise an alkylvinylidene isomer, in some cases, at least 50% and, in other cases, at least 70%, formed by methods such as described, for example, in U.S. Pat. No. 4,152,499, are suitable polyalkenes for use in forming the hydrocarbyl substituted hydroxyaromatic reactant. Also suitable for use in forming the long chain substituted hydroxyaromatic reactants herein are ethylene alpha-olefin copolymers having a number average molecular weight of 500 to 3,000, wherein at least about 30% of the polymer's chains contain terminal ethylidene unsaturation.

In one embodiment, the hydrocarbyl-substituted hydroxyaromatic compound has one R that is H, one R that is a C1-C4 alkyl group (in some approaches, a methyl group), and one R is a hydrocarbyl substituent having an average molecular weight in the range of about 300 to about 2,000, such as a polyisobutylene substituent. In other embodiments, the hydrocarbyl-substituted hydroxyaromatic compound can be obtained by alkylating o-cresol with a high molecular weight hydrocarbyl polymer, such as a hydrocarbyl polymer having a number average molecular weight between about 300 to about 2,000, to provide an alkyl-substituted cresol. In some instances, o-cresol is alkylated with polyisobutylene having a number average molecular weight between about 300 to about 2,000 to provide a polyisobutylene-substituted cresol. In yet other instances, o-cresol is alkylated with polyisobutylene (PIB) having a number average molecular weight between about 500 to about 1,500 to provide a polyisobutylene-substituted cresol (PIB-cresol).

In yet other approaches, the hydrocarbyl-substituted hydroxyaromatic compound can be obtained by alkylating o-phenol with a high molecular weight hydrocarbyl polymer, such as a hydrocarbyl polymer group having a number average molecular weight between about 300 to about 2,000, to provide an alkyl-substituted phenol. In one embodiment, o-cresol is alkylated with polybutylene having a number average molecular weight between about 500 to about 1,500 to provide a polybutylene-substituted cresol.

Alkylation of the hydroxyaromatic compound may be performed in the presence of an alkylating catalyst, such as a Lewis acid catalyst (e.g., $BF_3$ or $AlCl_3$), at a temperature of about 30 to about 200° C. For a polyolefin used as the hydrocarbyl substituent, it may have a polydispersity (Mw/Mn) of about 1 to about 4, in other cases, from about 1 to about 2, as determined by GPC. Suitable methods of alkylating the hydroxyaromatic compounds are described in GB 1,159,368 or U.S. Pat. Nos. 4,238,628; 5,300,701 and 5,876,468, which are all incorporated herein by references in their entirety.

Representative aldehyde sources for use in the preparation of the Mannich base products herein include aliphatic aldehydes, aromatic aldehydes, and/or heterocyclic aldehydes. Suitable aliphatic aldehydes may include C1 to C6 aldehydes, such as formaldehyde, acetaldehyde, propionaldehyde, butyraldehyde, valeraldehyde, and hexanal aldehyde. Exemplary aromatic aldehydes may include benzaldehyde and salicylaldehyde, and exemplary heterocyclic aldehydes may include furfural and thiophene aldehyde. In some instances, formaldehyde-producing reagents such as paraformaldehyde, or aqueous formaldehyde solutions such as formalin may also be used in forming the Mannich-based tertiary amines herein. Most preferred is formaldehyde and/or formalin.

To prepare the Mannich-based quaternary ammonium salt detergents herein, a Mannich reaction of the selected polyamine, the hydrocarbyl-substituted hydroxyaromatic compound, and the aldehyde as described above is first conducted at a temperature about 30° C. to about 200° C. The reaction can be conducted in bulk (no diluent or solvent) or in a solvent or diluent. Water is evolved and can be removed by azeotropic distillation during the course of the reaction. For instance the temperature is typically increased, such as to about 150° C., when removing the water that is evolved in the reaction. Typical reaction times range from about 3 to about 4 hours, although longer or shorter times can be used as necessary or as desired.

An exemplary Mannich reaction can start with the addition of a hydrocarbyl-substituted hydroxyaromatic component to the reaction vessel together with a suitable solvent to obtain a blend. The blend is mixed under an inert atmosphere. Next, the amine compound is added when the blend is homogeneous and is at a moderate temperature, such as about 40 to about 45° C. Then, the selected aldehyde, such as formaldehyde, is added. The temperature rises, such as to about 45 to about 50° C., and the temperature may be further increased to less than 100° C., such as about 80° C., and maintained at such temperature for about 30 minutes to about 60 minutes. Distillation can then be conducted using a Dean Stark trap or equivalent apparatus and the temperature is set to about 130 to about 150° C., and it should be appreciated that distillation may start after a period of time to allow the reaction mixture to reach about 95 to 105° C. The temperature is maintained at the selected elevated temperature for sufficient time, which may be about an additional 2 hours to about 2.5 hours to produce the Mannich-based tertiary amine. Other suitable Mannich reaction schemes may be used as well to prepare the intermediate Mannich-based tertiary amine. The so-formed Mannich-based tertiary amine is then alkylated or quaternized with a suitable alkylating or quaternizing agent as discussed herein.

In one approach or embodiment, an exemplary Mannich-based quaternary ammonium salt cation may have the structure of Formula VI (Formula VI)

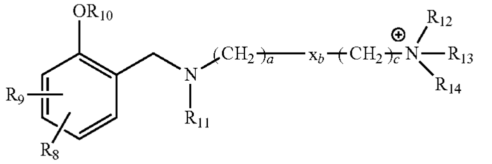

wherein $R_8$ is a hydrocarbyl radical where a number average molecular weight of the hydrocarbyl is about 200 to about 5,000; $R_9$ is hydrogen or a $C_1$-$C_6$ alkyl group; $R_{10}$ is hydrogen or, together with $R_{11}$, a —C(O)— group or a —$CH_2$— group forming a ring structure with the nitrogen atom closest to the aromatic ring; $R_{11}$ is one of hydrogen, $C_1$-$C_6$ alkyl, —$(CH_2)_a$—$NR_5R_6$, —$(CH_2)_a$— Aryl($R_1$)($R_2$)($OR_3$), or together with $R_{10}$, a —C(O)— group or a —$CH_2$— group forming a ring structure with the nitrogen atom closest to the aromatic ring; $R_{12}$, is $C_1$-$C_6$ alkyl; $R_{13}$ and $R_{14}$, independently, are $C_1$-$C_6$ alkyl; a is an integer from 1 to 10, b is an integer selected from either 0 or 1, and c is an integer from 0 to 10; X is oxygen or nitrogen (with other R groups herein as defined above in other paragraphs). Preferably, $R_{10}$ is hydrogen, a is 1 to 4 (most preferably 3), b is 0, c is 0, and each of $R_{12}$, $R_{13}$, and $R_{14}$ are a C1 to C4 (preferably a C1) alkyl group.

In one embodiment or approach, the quaternary ammonium salt fuel additive has the structure of Formula VI above wherein $R_8$ is a hydrocarbyl radical derived from a 500 to 1,500 number average molecular weight polyisobutylene polymer or oligomer, $R_9$ is hydrogen or a methyl group, $R_{10}$ and $R_{11}$ are each hydrogen; a is an integer from 1 to 4, and b and c are each 0. An exemplary structure of this Mannich-based quaternary ammonium salt embodiment is shown below in Formula VIa:

(Formula VIa)

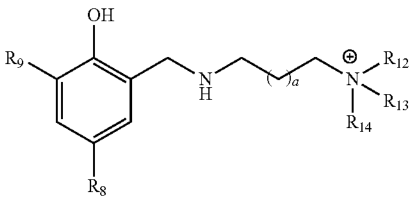

Amine Compound: In approaches or embodiments, the amine compound having at least one quaternizable ammonium group (e.g., tertiary amino group) suitable for forming the cations of the quaternary ammonium salt compound herein (e.g., reacting with either the hydrocarbyl-substituted polycarboxylic acid or anhydride herein; the Mannich reaction product discussed above; or other suitable compound) may be a wide variety of amine or polyamine compounds including, for instance, compounds having at least one oxygen or nitrogen group that is capable of reacting with the polycarboxylic acid or anhydride and/or Mannich reaction product, as needed, and also including at least one quaternizable amino group (e.g., a tertiary amine). In approaches, suitable amine compounds may have the general structure of the Formulas below:

(Formula VIIa)

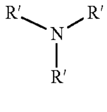

or (Formula VIIb)

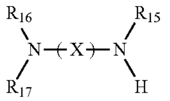

wherein each of R' thereof is independently selected from hydrocarbyl groups containing from 1 to 200 carbon atoms and where at least one R' group include at least one oxygen or nitrogen group capable of reacting with the polycarboxylic acid or anhydride. Alternatively, $R_{15}$ is hydrogen or an alkyl group (e.g., a C1 to C50 alkyl group), $R_{16}$ and $R_{17}$, are each independently, alkyl or a hydrocarbyl group (e.g., a C1 to C50 alkyl or hydrocarbyl group), X is a bivalent alkyl group or alkyl ether group, and n is an integer of 1. Each hydrocarbyl group R' may independently be linear, branched, substituted, cyclic, saturated, unsaturated, or contain one or more hetero atoms. Suitable alkyl or hydrocarbyl groups for the formulas above may include, but are not limited to alkyl groups, aryl groups, alkylaryl groups, arylalkyl groups, alkoxy groups, aryloxy groups, amido groups, ester groups, imido groups, and the like. Any of the foregoing hydrocarbyl groups may also contain hetero atoms, such as oxygen or nitrogen atoms as needed to react with the polycarboxylic acid or anhydride. Particularly suitable alkyl or hydrocarbyl groups may be linear or branched alkyl groups. Some representative examples of amine compounds of the above formulas, which can be used to form quaternary ammonium salt compounds of this disclosure include, but are not limited to, trimethyl amine, triethyl amine, tri-n-propyl amine, dimethylethyl amine, dimethyl lauryl amine, dimethyl oleyl amine, dimethyl stearyl amine, dimethyl eicosyl amine, dimethyl octadecyl amine, N-methyl piperidine, N,N'-dimethyl piperazine, N-methyl-N-ethyl piperazine, N-methyl morpholine, N-ethyl morpholine, N-hydroxyethyl morpholine, pyridine, triethanol amine, triisopropanol amine, methyl diethanol amine, dimethyl ethanol amine, lauryl diisopropanol amine, stearyl diethanol amine, dioleyl ethanol amine, dimethyl isobutanol amine, methyl diisooctanol amine, dimethyl propenyl amine, dimethyl butenyl amine, dimethyl octenyl amine, ethyl didodecenyl amine, dibutyl eicosenyl amine, triethylene diamine, hexamethylene tetramine, N,N,N',N'-tetramethylethylenediamine, N,N,N',N'-tetramethylpropylenediamine, N,N,N',N'-tetraethyl-1,3-propanediamine, methyldi-cyclohexyl amine, 2,6-dimethylpyridine, dimethyl-cylohexylamine, $C_{10}$-$C_{30}$-alkyl or alkenyl-substituted amidopropyldimethylamine, $C_{12}$-$C_{200}$-alkyl or alkenyl-substituted succinic-carbonyldimethylamine, succinimide deriviatives thereof, dimethylamino propylamine, dimethylaminoethoxy propylamine, N,N-dimethyl-dipropylene-triamine, and the like amine compounds. In approaches, if the amine compound contains solely primary or secondary amino groups, it is necessary to alkylate at least one of the primary or secondary amino groups to a tertiary amino group prior to the reaction with the suitable quaternizing agent.

In one particular approach or embodiment, a suitable amine compound to form the quaternary ammonium salt compounds of the present disclosure is an amine or polyamine compound having the structure of Formula VIII:

$$(R_{15})(H)N—(CH_2)_a—X_m—(CH_2)_b—X_n—(CH_2)_c—N(R_{16})(R_{17}) \quad \text{(Formula VIII)}$$

wherein each X is a bivalent moiety selected from —O—, —N(R)—, —C(O)—, —C(O)O—, or —C(O)N(R)—; each $R_{15}$ of Formula VIII is hydrogen or a hydrocarbyl group; each $R_{16}$ and $R_{17}$ of Formula VIII is, independently, a hydrocarbyl group; each R of Formula VIII if present is, independently, a hydrogen atom or a group selected from $C_{1-6}$ aliphatic, phenyl, or alkylphenyl; m and n of Formula VIII are, independently, integers of 0 or 1; and a, b, and c of Formula VIII are each, independently, an integer of 1 to 10. In one particular embodiment, both m and n of Formula VIII are each 0 and a, b, and c of Formula VIII are each 1. In another particular embodiment of Formula VIII, m is 1 and n is 0, X is —O—, and a is 3, b is 1, and c is 1.

In yet another embodiment, a suitable amine compound to form the cations of the present disclosure may have the structure of Formula IX $$R_{18}[OCH_2CHR]_n[OCHRCH_2]_mNR_{19}R_{19} \quad \text{(Formula IX)}$$

wherein each R of Formula IX if present is, independently, a hydrogen atom or a group selected from $C_{1-6}$ aliphatic, phenyl, or alkylphenyl; $R_{18}$ is a hydrocarbyl group, n of Formula IX is an integer of 1 to 20, m of Formula IX is an integer of 1 to 20, and each $R_{19}$ of Formula IX is, independently, hydrogen or a hydrocarbyl group.

In some embodiments, the amine or polyamine compound suitable for the quaternary ammonium cations herein is selected from dimethylaminoethoxy propylamine, dimethyldipropylenetriamine, dimethylamino propylamine, etheramines or polyetheramines, fatty amines or fatty polyamines, polyalkylene amines, and the like amines, or combinations thereof.

Fuel Additive Package, Concentrate, or Composition

In one particular approach, the quaternary ammonium salt compounds of this disclosure may be used in a fuel additive package, a fuel additive concentrate, or fuel additive composition that is suitable for use in fuels, such as gasoline or diesel. In embodiments, the above-described quaternary ammonium salt compounds may be employed in amounts sufficient to reduce or inhibit deposit formation in a fuel system, a combustion chamber of an engine and/or crankcase, and/or within fuel injectors. In some aspects, the fuel additive package (and fuel compositions including the fuel additive package) may contain minor amounts of the above described reaction product or resulting salt thereof that controls or reduces the formation of engine deposits, for example injector deposits in engines. For example, any embodiments of the fuel compositions (e.g., gasoline, diesel, etc.) of this disclosure may contain, on an active ingredient basis, an amount of the quaternary ammonium salt compound (or reaction product as described herein) in the range of about 1 ppm to about 100 ppm, in other approaches, about 3 ppm to about 50 ppm, in yet further approaches about 5 to about 45 ppm of the quaternary ammonium salt, or about 5 to about 40 ppm of the quaternary ammonium salt, or about 5 ppm to about 25 ppm of the quaternary ammonium salt.

In other embodiments where the fuel is gasoline, an amount of the quaternary ammonium salt compound (or reaction product as described herein) may be in the range of about 1 ppm to about 100 ppm, in other approaches, about 3 ppm to about 50 ppm, in yet further approaches about 4 ppm to about 45 ppm, or about 5 to about 45 ppm of the quaternary ammonium salt is used. In other embodiments where the fuel is diesel, an amount of the quaternary ammonium salt compound (or reaction product as described herein) may be in the range of about 1 ppm to about 200 ppm, in other approaches, about 10 ppm to about 100 ppm, in yet further approaches about 20 ppm to about 60 ppm of the quaternary ammonium salt, and in yet further approaches about 30 ppm to 50 ppm of the quaternary ammonium salt is used. It will also be appreciated that any endpoint between the above-described ranges are also suitable range amounts as needed for a particular application. The active ingredient basis excludes the weight of (i) unreacted components associated with and remaining in the product as produced and used, and (ii) solvent(s), if any, used in the manufacture of the product either during or after its formation.

In yet other embodiments, any embodiment of the quaternary ammonium salt compounds of this disclosure may provide to a fuel composition about 1 to about 100 ppm of a cation (in other approaches where the fuel is gasoline, about 3 ppm to about 50 ppm of a cation, or about 5 ppm to about 30 ppm of a cation, or about 10 to about 25 ppm of a cation, or about 10 to about 20 ppm of a cation (or any other ranges therebetween); and in other approaches where the fuel is diesel, about 5 ppm to about 80 ppm of a cation, or about 10 ppm to about 50 ppm of a cation, or about 10 to about 45 ppm of a cation, or about 20 to about 40 ppm of a cation, or about 20 to about 30 ppm of a cation (or any other ranges therebetween)) and about 1 ppm to about 100 ppm of an anion (in other approaches where the fuel is gasoline, about 3 ppm to about 30 ppm of an anion, or about 5 ppm to about 25 ppm of an anion, or about 5 to about 16 ppm of an anion (or any other ranges therebetween); and in other approaches where the fuel is diesel, about 5 ppm to about 80 ppm of an anion, or about 10 ppm to about 50 ppm of an anion, or about 10 to about 25 ppm of an anion (or any other ranges therebetween)). The anion or the cation may be any embodiment as described in this disclosure.

Other Additives

In the context of an embodiment of the quaternary ammonium salt compound used as a fuel additive, one or more optional compounds may also be present in the fuel additive packages or the fuel compositions herein in combination with the quaternary ammonium salt fuel additives of this disclosure. For example, the fuel additive packages or fuels herein may contain conventional quantities of cetane improvers, octane improvers, corrosion inhibitors, cold flow improvers (CFPP additive), pour point depressants, solvents, demulsifiers, lubricity additives, friction modifiers, amine stabilizers, combustion improvers, detergents, dispersants, antioxidants, heat stabilizers, conductivity improvers, metal deactivators, marker dyes, organic nitrate ignition accelerators, cyclomatic manganese tricarbonyl compounds, carrier fluids, and the like. In some aspects, the compositions described herein may contain about 10 weight percent or less, or in other aspects, about 5 weight percent or less, based on the total weight of the additive concentrate, of one or more of the above additives. Similarly, the fuels may contain suitable amounts of conventional fuel blending components such as methanol, ethanol, dialkyl ethers, 2-ethylhexanol, and the like.

In some aspects of the disclosed embodiments, organic nitrate ignition accelerators that include aliphatic or cycloaliphatic nitrates in which the aliphatic or cycloaliphatic group is saturated, and that contain up to about 12 carbons may be used. Examples of organic nitrate ignition accelerators that may be used are methyl nitrate, ethyl nitrate, propyl nitrate, isopropyl nitrate, allyl nitrate, butyl nitrate, isobutyl nitrate, sec-butyl nitrate, tert-butyl nitrate, amyl nitrate, isoamyl nitrate, 2-amyl nitrate, 3-amyl nitrate, hexyl nitrate, heptyl nitrate, 2-heptyl nitrate, octyl nitrate, isooctyl nitrate, 2-ethylhexyl nitrate, nonyl nitrate, decyl nitrate, undecyl nitrate, dodecyl nitrate, cyclopentyl nitrate, cyclohexyl nitrate, methylcyclohexyl nitrate, cyclododecyl nitrate, 2-ethoxyethyl nitrate, 2-(2-ethoxyethoxy)ethyl nitrate, tetrahydrofuranyl nitrate, and the like. Mixtures of such materials may also be used.

Examples of suitable optional metal deactivators useful in the compositions of the present application are disclosed in U.S. Pat. No. 4,482,357, the disclosure of which is herein incorporated by reference in its entirety. Such metal deactivators include, for example, salicylidene-o-aminophenol, disalicylidene ethylenediamine, disalicylidene propylenediamine, and N,N'-disalicylidene-1,2-diaminopropane.

Suitable optional cyclomatic manganese tricarbonyl compounds which may be employed in the compositions of the present application include, for example, cyclopentadienyl manganese tricarbonyl, methylcyclopentadienyl manganese tricarbonyl, indenyl manganese tricarbonyl, and ethylcyclopentadienyl manganese tricarbonyl. Yet other examples of suitable cyclomatic manganese tricarbonyl compounds are disclosed in U.S. Pat. Nos. 5,575,823 and 3,015,668 both of which disclosures are herein incorporated by reference in their entirety.

Other commercially available detergents may be used in combination with the reaction products described herein. Such detergents include but are not limited to succinimides, Mannich base detergents, quaternary ammonium detergents, bis-aminotriazole detergents as generally described in U.S. patent application Ser. No. 13/450,638, and a reaction product of a hydrocarbyl substituted dicarboxylic acid, or anhydride and an aminoguanidine, wherein the reaction product has less than one equivalent of amino triazole group per molecule as generally described in U.S. patent application Ser. Nos. 13/240,233 and 13/454,697.

The additives of the present application, including the quaternary ammonium salts described above, and optional additives used in formulating the fuels of this invention may be blended into the base fuel individually or in various sub-combinations. In some embodiments, the additive components of the present application may be blended into the fuel concurrently using an additive concentrate, as this takes advantage of the mutual compatibility and convenience afforded by the combination of ingredients when in the form of an additive concentrate. Also, use of a concentrate may reduce blending time and lessen the possibility of blending errors.

Fuels or Fuel Compositions

The fuels or fuel compositions of the present application including at least the quaternary ammonium salt compound (or an additive packing that includes the quaternary ammonium salt fuel additive) as described herein may be applicable to the operation of diesel, jet, or gasoline engines. In one approach, the quaternary ammonium salts fuel additives herein are well suited for diesel or gasoline. In one embodiment, the fuel is diesel fuel. In another embodiment, the fuel is gasoline. In yet another embodiment, the fuel is a jet fuel. The fuels may include any and all middle distillate fuels, diesel fuels, biorenewable fuels, biodiesel fuel, fatty acid alkyl ester, gas-to-liquid (GTL) fuels, gasoline, jet fuel, alcohols, ethers, kerosene, low sulfur fuels, synthetic fuels, such as Fischer-Tropsch fuels, liquid petroleum gas, bunker oils, coal to liquid (CTL) fuels, biomass to liquid (BTL) fuels, high asphaltene fuels, fuels derived from coal (natural, cleaned, and petcoke), genetically engineered biofuels and crops and extracts therefrom, and natural gas. "Biorenewable fuels" as used herein is understood to mean any fuel which is derived from resources other than petroleum. Such resources include, but are not limited to, corn, maize, soybeans and other crops; grasses, such as switchgrass, miscanthus, and hybrid grasses; algae, seaweed, vegetable oils; natural fats; and mixtures thereof. In an aspect, the biorenewable fuel can comprise monohydroxy alcohols, such as those comprising from 1 to about 5 carbon atoms. Non-limiting examples of suitable monohydroxy alcohols include methanol, ethanol, propanol, n-butanol, isobutanol, t-butyl alcohol, amyl alcohol, and isoamyl alcohol. Preferred fuels include diesel fuels.

The fuels herein are suitable for use in various internal combustion systems or engines. The systems or engines may include both stationary engines (e.g., engines used in electrical power generation installations, in pumping stations, etc.) and ambulatory engines (e.g., engines used as prime movers in automobiles, trucks, road-grading equipment, military vehicles, etc.). By combustion system or engine herein is meant, internal combustion engines, for example and not by limitation, Atkinson cycle engines, rotary engines, spray guided, wall guided, and the combined wall/spray guided direct injection gasoline ("DIG" or "GDI") engines, turbocharged DIG engines, supercharged DIG engines, homogeneous combustion DIG engines, homogeneous/stratified DIG engines, DIG engines outfitted with piezoinjectors with capability of multiple fuel pulses per injection, DIG engines with EGR, DIG engines with a lean-NOx trap, DIG engines with a lean-NOx catalyst, DIG engines with SN-CR NOx control, DIG engines with exhaust diesel fuel after-injection (post combustion) for NOx control, DIG engines outfitted for flex fuel operation (for example, gasoline, ethanol, methanol, biofuels, synthetic fuels, natural gas, liquefied petroleum gas (LPG), and mixtures thereof.) Also included are conventional and advanced port-fueled internal combustion engines, with and without advanced exhaust after-treatment systems capability, with and without turbochargers, with and without superchargers, with and without combined supercharger/turbocharger, with and without on-board capability to deliver additive for combustion and emissions improvements, and with and without variable valve timing. Further included are gasoline fueled homogeneous charge compression ignition (HCCI) engines, diesel HCCI engines, two-stroke engines, diesel fuel engines, gasoline fuel engines, stationary generators, gasoline and diesel HCCI, supercharged, turbocharged, gasoline and diesel direct injection engines, engines capably of variable valve timing, leanburn engines, engines capable of inactivating cylinders or any other internal combustion engine. Still further examples of combustion systems include any of the above-listed systems combined in a hybrid vehicle with an electric motor.

Accordingly, aspects of the present application are directed to methods of or the use of the quaternary ammonium fuel additives herein for reducing injector deposits in an internal combustion system or engine or within a fuel system for an internal combustion system or engine, cleaning-up fouled injectors, or un-sticking injectors. The methods include combusting in an internal combustion engine a fuel containing the above-described quaternary ammonium salt detergent. In another aspect, the quaternary ammonium fuel additives described herein or fuel containing the quaternary ammonium compounds herein may be combined with one or more of polyhydrocarbyl-succinimides, -acids, -amides, -esters, -amide/acids and -acid/esters, reaction products of polyhydrocarbyl succinic anhydride and aminoguanidine and its salts, Mannich compounds, and mixtures thereof. In other aspects, the methods or use include injecting a hydrocarbon-based fuel comprising a quaternary ammonium salt fuel additive of the present disclosure through the injectors of the engine into the combustion chamber, and igniting the fuel to prevent or remove deposits on fuel injectors, to clean-up fouled injectors, and/or to unstick injectors. In some aspects, the internal combustion engine is a gasoline engine, e.g., Port Fuel Injector (PFI) engine or direct injection engine. In some aspects, the internal combustion engine is a diesel engine, which can be either a direct injection engine or indirect injection engine. A non-limiting example of direct injection diesel engine is a common rail injection system, in which the fuel is compressed utilizing a high-pressure pump that supplies it to the fuel injection valves through a common rail. Another non-limiting example is a unit injection system which integrates the high-pressure pump and fuel injection valve in one assembly, achieving the highest possible injection pressures exceeding 2000 bar (2×10 8<Pa). In both systems, in pressurizing the fuel, the fuel gets hot, often to temperatures around 100° C., or above. In still some aspects, the present invention is related to reduction of external deposits (deposits on the injector tip) and internal diesel injector deposits (IDID). It is widely recognized that deposits in the spray channels can lead to a reduction in fuel flow and thus to power loss, and deposits on the injector tip, on the other hand, impair the optimal formation of fuel spray mist and thereby cause poorer combustion and the associated higher emissions and increased fuel consumption. In some aspects, the method may also comprise mixing into the fuel at least one of the optional additional ingredients described above.

Another aspect of the present application is a method of improving performance of an internal combustion engine (examples of which are described above) using the quaternary ammonium fuel additives herein. The improved performance includes power gains, reduced particulate emissions, reduced fuel consumption, improved combustion, and/or improved fuel economy.

Selected Definitions

The molecular weight for any embodiment herein may be determined with a gel permeation chromatography (GPC) instrument obtained from Waters or the like instrument and the data was processed with Waters Empower Software or the like software. The GPC instrument may be equipped with a Waters Separations Module and Waters Refractive Index detector (or the like optional equipment). The GPC operating conditions may include a guard column, 4 Agilent PLgel columns (length of 300×7.5 mm; particle size of 5μ, and pore size ranging from 100 to 10000 Å) with the column temperature at about 40° C. Unstabilized HPLC grade tetrahydrofuran (THF) may be used as solvent, at a flow rate of 1.0 mL/min. The GPC instrument may be calibrated with commercially available polystyrene (PS) standards having a narrow molecular weight distribution ranging from 500 to 380,000 g/mol. The calibration curve can be extrapolated for samples having a mass less than 500 g/mol. Samples and PS standards can be in dissolved in THF and prepared at concentration of 0.1 to 0.5 wt. % and used without filtration. GPC measurements are also described in U.S. Pat. No. 5,266,223, which is incorporated herein by reference. The GPC method additionally provides molecular weight distribution information; see, for example, W. W. Yau, J. J. Kirkland and D. D. Bly, "Modern Size Exclusion Liquid Chromatography", John Wiley and Sons, New York, 1979, also incorporated herein by reference.

As used herein, the term "hydrocarbyl group" or "hydrocarbyl" is used in its ordinary sense, which is well-known to those skilled in the art. Specifically, it refers to a group having a carbon atom directly attached to the remainder of a molecule and having a predominantly hydrocarbon character. Examples of hydrocarbyl groups include: (1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical); (2) substituted hydrocarbon substituents, that is, substituents containing non-hydrocarbon groups which, in the context of the description herein, do not alter the predominantly hydrocarbon substituent (e.g., halo (especially chloro and fluoro), hydroxy, alkoxy, mercapto, alkylmercapto, nitro, nitroso, amino, alkylamino, and sulfoxy); (3) hetero-substituents, that is, substituents which, while having a predominantly hydrocarbon character, in the context of this description, contain other than carbon in a ring or chain otherwise composed of carbon atoms. Hetero-atoms include sulfur, oxygen, nitrogen, and encompass substituents such as pyridyl, furyl, thienyl, and imidazolyl. In general, no more than two, or as a further example, no more than one, non-hydrocarbon substituent will be present for every ten carbon atoms in the hydrocarbyl group; in some embodiments, there will be no non-hydrocarbon substituent in the hydrocarbyl group.

As used herein, the term "major amount" is understood to mean an amount greater than or equal to 50 weight percent, for example from about 80 to about 98 weight percent relative to the total weight of the composition. Moreover, as used herein, the term "minor amount" is understood to mean an amount less than 50 weight percent relative to the total weight of the composition.

EXAMPLES

The following examples are illustrative of exemplary embodiments of the disclosure. In these examples as well as elsewhere in this application, all ratios, parts, and percentages are by weight unless otherwise indicated. It is intended that these examples are being presented for the purpose of illustration only and are not intended to limit the scope of the invention disclosed herein. Unless apparent based on the context of its use, reference to any standardized test method in the claims, disclosure, or these Examples refers to the version of the test method publicly available at the time of this disclosure.

Example 1

For this example, 30.25 g (0.2563 mol) of dimethyl oxalate (DMO) was added to 93.82 g (0.2563 mol) of Radialube® 7930 (N-(3-dimethylaminopropyl oleamide, hereinafter also referred to as OD), which is the amide formed from oleic acid and 3-dimethylaminopropylamine (DMAPA). Addition was carried out at room temperature (about 20 to about 25° C.) in a glass pressure reactor. The reactor was sealed and the mixture was subsequently heated to 70° C. in an oven and shaken until homogeneous. It was then maintained at 70° C. overnight for 17 hours, after which the temperature was raised to 90° C. for an additional 24 hrs. Upon cooling, the product was recovered in quantitative yield as a yellow, waxy solid. Quantitative Carbon NMR was used to confirm complete conversion, noting the presence of quaternized product (OD-Quat) and monomethyl oxalate (MMO), and also noting the absence of DMO and of the dimethylamino group of DMAPA.

Example 2 (Inventive)

To 30.27 g (0.0625 mol) of the product from Example 1 was added, 13.58 g (0.0631 mol) of Tomamine® PA-14 (96% active 3-(iso-decyloxy)-propylamine, available from Evonik Corp.) and 43.85 g of Naphthalene-depleted Aromatic 150 Solvent in a sealed glass pressure reactor. The mixture was homogenized at 50° C. and held at that temperature for 10 days. Carbon NMR showed partial conversion, so the temperature was raised to 70° C. After one week the product was recovered in quantitative yield as a reddish amber liquid. Quantitative Carbon NMR was used to confirm 89% conversion of MMO to the PA-14 amide-acetate, with no observed residual Tomamine® PA-14. An additional 10% Tomamine® PA-14 pushed the conversion up to 94% after 3 additional days at 70° C.

Example 3

For this example, 113.59 g of a Polyisobutenyl Succinic Anhydride (PIBSA) was aminated using 9.78 g of DMAPA (dimethylaminopropylamine) at 140° C. for 4 hours while removing water and excess amine. The final formed PIBSI (119.88 g) had a nominal molecular weight (nominal MW) of 1470, as determined by Total Base Number (TBN). To 16.35 g (0.011 mol) of this product was charged, 1.313 g (0.011 mol) of dimethyl oxalate (DMO) in a sealed glass pressure reactor. The mixture was homogenized at 90° C. and stored in an oven at that temperature for two days. The yield is quantitative. Quantitative Carbon NMR was used to confirm nearly complete conversion to the quaternary ammonium salt with mono-methyl oxalate (MMO) as the anion.

Example 4 (Inventive)

To 4.8241 g (3.037 mmol) of the product from Example 3 was added, 0.6645 g (3.085 mmol) of Tomamine® PA-14 and 4.8307 g of Naphthalene-Depleted Aromatic 150 Solvent in a sealed glass pressure reactor. The reaction mixture was homogenized and stored at 70° C. for seven days. After cooling the product was recovered in quantitative yield as a reddish amber liquid. Quantitative Carbon NMR was used to confirm 91% conversion of MMO to the PA-14 amide-acetate, with no observed residual Tomamine® PA-14.

Example 5

Using the procedure as described in Example 3 above, a quaternized PIBSI made from dimethylaminoethoxypropylamine (DMAEPA) was prepared at an activity of 50% in Aromatic Solvent. The equivalents of MMO in the product was determined to be 4.54 g per 100 g. Quantitative Carbon NMR was used to confirm greater than 98% conversion of amine to the quaternary ammonium salt with MMO as the sole anion.

Example 6 (Inventive)

To 566.81 g of the product from Example 5 was added, 64.44 g (0.2992 mol, 1.15 eq) of Tomamine® PA-14. The mixture was heated to 90° C. in an oven for 5 days. Quantitative Carbon NMR was used to confirm 94% conversion of MMO to the PA-14 amide-acetate, with no observed residual Tomamine® PA-14.

Example 7 (Inventive)

A novel amide-ester methylating agent was prepared by reacting 89.00 g (0.4132 mol) of Tomamine® PA-14 with 48.58 g (0.4113 mol) of dimethyl oxalate (DMO) dissolved in 200 g of methanol, at −20° C. The amine was dropped into a partly soluble solution of DMO over a period of one-half hour while stirring vigorously. The resultant orange solution was allowed to warm overnight. It was then concentrated on a rotary evaporator under vacuum at 50° C. to yield 123.64 g of an orange fluid. As determined by Quantitative Carbon NMR, the mixture contained a small amount of DMO. The excess DMO was consumed by adding an additional 5.43 g of Tomamine® PA-14. After two days at room temperature, the product mixture was found to contain 89 mole-percent of the intended amide-ester, with 8 mol-% of the symmetrical diamide and 3 mol-% residual DMO.

Example 8 (Inventive)

To 24.70 g (0.0675 mol) of Radialube® 7930 (OD) was charged, a total of 28.94 g of the product from Example 7 above in a sealed glass pressure reactor. The mixture was homogenized at 90° C. and stored in an oven at that temperature for seven days. The yield of coupled cationic and anionic surfactants was quantitative.

Example 9 (Inventive)

A novel amide-ester methylating agent was prepared by reacting 98.70 g (0.4561 mol) of Tomamine® PA-14 with 48.98 g (0.4147 mol) of DMO dissolved in 200 g of tetrahydrofuran (THF), at 0° C. The amine was dropped into a solution of dimethyl oxalate (DMO) over a period of one-half hour while stirring vigorously. After one hour at 0° C. the resultant orange solution was allowed to warm to room temperature. After two hours, a 1.337 g sample was removed for analysis. The mole ratio of amide-ester to symmetrical diamide was approximately 9:1. To the warm solution was added, 27.28 g (0.1867 mol) of dimethyl-ethoxy-propylamine (DMAEPA), dropwise over a 15-minute period. The temperature rose from 20 to 29° C. After 3 hours, a 1.887 g sample was removed for analysis. Following that, solvent was removed on a rotary evaporator at 70° C., under vacuum, over a period of one hour. The final temperature was 90° C. The recovered mass was 154.49 g of a red viscous oil. This oil was stored in a 90° C. oven for 65 hours. As determined by Quantitative Carbon NMR, the mixture was found to be free of unreacted dimethylamino groups, which had been converted to quaternary ammonium cation.

Example 10

Diesel Clean-up Evaluation: Inventive and Comparative additives described above were evaluated for injector clean-up performance in a diesel engine using the DW-10B diesel engine test, also known as the CEC F-98-08 test. This is a standardized European test designed to evaluate the propensity of diesel fuels to cause injector fouling and the effectiveness of fuel additives in preventing this issue. The engine undergoes multiple cycles, with 4-hour soak periods in between, until a total of 32 hours of testing is completed or until injector coking occurs. A cycle consists of 12 steady-state conditions, each lasting for a specific duration, to simulate real-world driving conditions. Fouling is indicated by a significant loss of power, rough idling, or engine failure to start.

The DW-10B test uses a Peugeot DW-10 engine, which is a 2.0-liter, 4-cylinder, turbocharged, direct injection diesel engine equipped with a high-pressure common rail fuel system. The engine is mounted on a test bench and operated under controlled conditions. The goal of the testing was to evaluate the effectiveness of deposit control additives (DCAs) in preventing or removing injector deposits, so the test was run in two back-to-back phases: Phase I: Fouling on a low-sulfur Diesel base fuel (e.g., Table 1 below) dosed with 1 ppm of zinc to accelerate injector fouling. Phase II: Clean-up on fuel additized with inventive and comparative quaternary ammonium salt additives of Table 2.

TABLE 1

Ultra-Low-Sulfur Diesel Fuel

| TEST PARAMETER | ASTM METHOD | TEST RESULT | UNITS |
|---|---|---|---|
| Alkyl Nitrate | D4046 | 0.03 | Volume % |
| API Gravity (15° C.) | D4052 | 37.0 | API |
| Specific Gravity (15° C.) | D4052 | 0.8398 | water |
| Density (15° C.) | D4052 | 0.8389 | g/mL |
| BTU/lb (gross) | D240 | 19656 | BTU |
| BTU/lb (net) | D240 | 18447 | BTU |
| Carbon | D5291 | 86.75 | Weight % |
| Hydrogen | D5291 | 13.25 | Weight % |
| Cetane Index (proc A) | D4737 | 49.8 | n.a. |
| Cetane Number | D613 | 46.2 | n.a. |
| Flashpoint | D93 | 141.8 | ° F. |
| Aromatics | D1319 | 21.9 | Volume % |
| Olefins | D1319 | 1.1 | Volume % |
| Saturates | D1319 | 77.0 | Volume % |
| Kinematic Viscosity (40° C.) | D445 | 2.562 | centistokes |
| Filterable Insolubles | D2274, D6468 | <0.1 | mg/mL |
| Adherent Insolubles | D2274, D6468 | <0.1 | mg/mL |
| Total Insolubles | D2274, D6468 | <0.1 | mg/mL |
| Sediment & Water | D2709 | <0.025 | Volume % |
| Sulfur | D5453 | 8.3 | ppm |
| Cloud point | D5773 | 8.6 | ° F. |
| CFPP | D6371 | −13.0 | ° C. |
| Pour point | D5949 | −5.8 | ° F. |
| HERR (60° C.) | D6079 | 580 | um |
| FAME | D7371 | <1.00 | Volume % |
| Distillation | D86 | Degrees | |
| IBP | | 324.6 | ° F. |
| 5% | | 375.9 | ° F. |
| 10% | | 398.3 | ° F. |
| 20% | | 429.8 | ° F. |
| 30% | | 456.8 | ° F. |
| 40% | | 481.8 | ° F. |
| 50% | | 505.6 | ° F. |
| 60% | | 530.2 | ° F. |
| 70% | | 556.8 | ° F. |
| 80% | | 585.8 | ° F. |
| 90% | | 624.9 | ° F. |
| 95% | | 659.1 | ° F. |
| EP | | 672.4 | ° F. |
| Recovery | D86 | 97.4 | % |
| Residue | D86 | 1.4 | % |
| Loss | D86 | 1.2 | % |
| PNA MIDDLE DISTILLATES | D6591 | Percent | |
| Paraffins | | 34.1 | % |
| Monocycloparaffins | | 22.6 | % |
| Dicycloparaffins | | 21.9 | % |
| Tricycloparaffins | | 7.8 | % |
| Alkylbenzenes | | 3.1 | % |
| Indanes/Tetralins | | 5.3 | % |
| Indenes | | 2.6 | % |
| Naphthalenes | | 1.2 | % |
| Acenaphthenes | | 0.7 | % |
| Acenaphthalenes | | 0.5 | % |
| Tricyclic aromatics | | 0.2 | % |
| Total | | 100.0 | % |

A summary of the DW-10B injector clean-up performance of this Example is presented in Table 2 below using Inventive additives 2, 8, and 9 and Comparative additive 1. While both the inventive and comparative additives demonstrated clean-up performance on this test platform and in the selected test fuel, the time required to achieve clean-up and the equilibrated end-of-test final power was better for inventive additives. For example, it is common in this test for additives to cross the zero line, and thus show improved power; however, only Inventive Examples 8 and 2 provided improved power by crossing the zero line. Here, Example 1 did not achieve greater than −3% power. Directly comparative are the results from Inventive Examples 8 and 2 with Example 1, which are tests of exactly the same quaternary ammonium cation (e.g., a methylated OD) but with inventive anions. Example 1 had as its anion monomethyl oxalate, which cannot act as a surfactant. On the other hand, Inventive Examples 8 and 2 included the novel Tomamine® PA-14/DMO-derived anion, and this new anion resulted in a faster clean-up (roughly 3 hours for Inventive Example 8 and 2 hours for Inventive Example 2, versus 15 hours for Comparative Example 1).

TABLE 2

DW-10B injector Clean-up Performance Measured on the Peugeot Engine

| Additive | Status | Total Quat Salt Treat Rate | Cation | Anion | SOT/EOT* % Power |
|---|---|---|---|---|---|
| Example 9 | Inventive | 40 ppm | 24 ppm | 16 ppm | −5.23/−1.63 |
| Example 1 | Comparative | 29 ppm | 24 ppm | 5 ppm | −7.57/−3.32 |
| Example 8 | Inventive | 40 ppm | 19 ppm | 21 ppm | −6.33/+1.27 |
| Example 2 | Inventive | 45 ppm | 24 ppm | 21 ppm | −5.11/0.39 |

*SOT = Start of test and EOT = End of test

As noted in Table 2 above, Comparative Example 1 was treated at 29 ppm to deliver 24 ppm of the active cationic surfactant to the fuel (and only 5 ppm of anion), whereas Inventive Example 8 was treated at 40 ppm in order to deliver just 19 ppm of active cationic surfactant to the fuel. Clearly, the anionic counterion of the additive surprisingly impacts the performance at a treat rate of roughly 21 ppm in the fuel. Example 2 was treated to deliver 45 ppm of the active quaternary ammonium detergent (and about 24 ppm of cation and about 21 ppm of anion).

FIG. 1 shows a comparison between the additive from Comparative Example 1 used at 29 ppm (e.g., 24 ppm of cation and 5 ppm of anion) and that from Inventive Example 8 used at 40 ppm (e.g., 19 ppm of cation and 21 ppm of anion). FIG. 1 shows the inventive Example 8 crosses the zero-line after just 3 hours whereas Inventive Example 1 never improves to beyond a −3% power loss and shows a performance lag or delay of over 6 hours from the start of the testing. Likewise, FIG. 2 shows the comparison between Inventive Example 2 and Comparative Example 1. Inventive Example 2 crosses the −1% power change just after 2 hours whereas Comparative Example 1 never improves to beyond −3% power loss and also shows a lag or performance delay from SOT lasting about 6 hours. FIGS. 1 and 2, therefore, provide factual evidence of the dramatic impact of anion counterion selection of the present disclosure on power recovery.

Example 11

Gasoline Clean-Up Evaluation: Injector clean-up in gasoline was evaluated using the GM LHU Top Tier gasoline injector keep-clean test. The test uses a GM LHU engine, which is a 2.0-liter, 4-cylinder, turbocharged, direct injection gasoline engine. This engine is representative of modern gasoline direct-injection (GDI) engines used in various GM vehicles. The engine is mounted on a test bench and operated under conditions as follows:

| Parameter | Min | Max |
|---|---|---|
| Dyno Speed [rpm] | 1985 | 2015 |
| Manifold Pressure [kPa] | 85 | 91 |
| Intake Air Pressure [kPa] | 0.04 | 0.06 |
| Engine Coolant Pressure [kPa] | 89 | 90 |
| Fuel Rail Pressure [kPa] | 445 | 460 |
| Exhaust Back Pressure [kPa] | 101 | 105 |
| Oil Gallery Temperature [° C.] | 86 | 88 |
| Engine Coolant Out Temperature [° C.] | 78 | 82 |
| Intake Air Temperature [° C.] | 31 | 33 |
| Fuel Rail Temperature [° C.] | 24 | 27 |
| Post Intercooler Boost Temperature [° C.] | 33 | 39 |
| Dew Point Temperature [° C.] | 14 | 17 |
| Coolant Flow [L/min] | 43 | 46 |

Inventive and Comparatives of this disclosure were also tested for their ability to restore injector cleanliness and ensure optimal engine performance in gasoline engines. The primary goal was to evaluate the effectiveness of the deposit control additives (DCAs) in removing injector deposits, so the test was run in two back-to-back phases: Phase I: Fouling on a non-ethanol (E0) standard base fuel used in the Sequence VH test (SVGM2, Tables 3a and 3b below). Our target dirty-up was reached after 60 hours of steady-state operation (2000 RPM and 100 NM), before changing to the additized fuel. Phase II: Clean-up lasting up to 48 hours on fuel additized with different active Inventive and Comparative additives. Time to 100% clean-up is one measure of performance, fast clean-up being preferred.

TABLE 3a

E0 Haltermann SVGM2, Sequence VH Test Fuel

| TEST PARAMETER | ASTM METHOD | TEST RESULT | UNITS |
|---|---|---|---|
| API Gravity (15° C.) | D4052 | 56.8 | API |
| Specific Gravity (15° C.) | D4052 | 0.7515 | rel. water |
| Density (15° C.) | D4052 | 0.7507 | g/mL |
| Benzene | D5769 | n.a. | % |
| BTU/lb (gross) | D240 | n.a. | BTU |
| BTU/lb (net) | D240 | 18501 | BTU |
| Carbon | D5291 | 86.3 | Weight % |
| Hydrogen | D5291 | 13.7 | Weight % |
| Aromatics | D1319 | 30.8 | Volume % |
| Olefins | D1319 | 6.6 | Volume % |
| Saturates | D1319 | 62.6 | Volume % |
| Sulfur | D5453 | 54.0 | ppm |
| HFRR (20° C.) | D6079 | n.a. | micrometer |
| Existent UNWASHED | D381 | 2.5 | mg/100 mL |
| Existent WASHED | D381 | 0.5 | mg/100 mL |
| OXIDATION, minutes | D525 | 1440+ | minutes |
| Ethanol | D5599 | n.a. | Volume % |
| Oxygen Content | D5599 | n.a. | % |
| RVP | D5191 | 8.9 | psi |
| RON | D2699 | 97.8 | n.a. |
| MON | D2700 | 88.4 | n.a. |
| (R + M)/2 | Calculation | 93.1 | n.a. |
| Distillation | D86 | Degrees | |
| IBP | | 88.3 | ° F. |
| 5% | | 111.6 | ° F. |
| 10% | | 129 | ° F. |
| 20% | | 157.1 | ° F. |
| 30% | | 187.7 | ° F. |
| 40% | | 215.1 | ° F. |
| 50% | | 231.6 | ° F. |
| 60% | | 244.4 | ° F. |
| 70% | | 261.5 | ° F. |
| 80% | | 302.9 | ° F. |
| 90% | | 344.7 | ° F. |
| 95% | | 361.4 | ° F. |
| EP | | 396 | ° F. |

TABLE 3a-continued

| E0 Haltermann SVGM2, Sequence VH Test Fuel | | | |
|---|---|---|---|
| Recovery | D86 | 96.5 | % |
| Residue | D86 | 1.1 | % |
| Loss | D86 | 2.4 | % |

TABLE 3b

| Detailed Hydrocarbon Analysis (ASTM D6733) | |
|---|---|
| | Weight % |
| Paraffins | 4.4 |
| Isoparrafins | 60.97 |
| Olefins | 5.59 |
| Naphthenes | 4.61 |
| Aromatics | 23.83 |
| Oxygenates | 0.0 |
| Unclassified | 0.6 |
| Total | 100.0 |

A summary of GDI injector clean-up performance is presented in Table 4 below. While all evaluated additives of this Example demonstrated 100% clean-up performance, the time required to achieve 100% clean-up performance was much better for Inventive additives. Directly comparative are the results from Inventive Example 8 and Comparative Example 1, which are tests of exactly the same quaternary ammonium cation (e.g., a methylated OD) but different anionic counterions. The additive of Comparative Example 1 had as its anion monomethyl oxalate (MMO), which cannot act as a surfactant. On the other hand, Inventive Example 8 had the Tomamine® PA-14/DMO-derived anion, and this surprisingly resulted in a dramatically faster clean-up (e.g., 100% clean-up in about half the time or roughly 9 hours for Inventive Example 8 versus about 18 hours for Comparative Example 1).

TABLE 4

GDI injector Clean-up Measured on the GM LHU Top Tier Test Engine

| Additive | Status | Treat Rate | Cation | Anion | % Clean-Up | Time to 100% |
|---|---|---|---|---|---|---|
| Example 9 | Inventive | 40 ppm | 24 ppm | 16 ppm | 100 | 4 h:58 m |
| Example 8 | Inventive | 40 ppm | 19 ppm | 21 ppm | 100 | 9 h:2 m |
| Example 1 | Comparative | 29 ppm | 24 ppm | 5 ppm | 100 | 17 h:43 m |

As noted in Table 4 above, Comparative Example 1 was treated at 29 ppm in order to deliver 24 ppm of the active cationic surfactant to the fuel and 5 ppm of the anion, whereas Inventive Example 8 was treated at 40 ppm in order to deliver 19 ppm of active cationic surfactant to the fuel and about 21 ppm of the anion. Thus, the anionic surfactant impacts performance in the fuel.

It is noted that, as used in this specification and the appended claims, the singular forms "a," "an," and "the," include plural referents unless expressly and unequivocally limited to one referent. Thus, for example, reference to "an antioxidant" includes two or more different antioxidants. As used herein, the term "include" and its grammatical variants are intended to be non-limiting, such that recitation of items in a list is not to the exclusion of other like items that can be substituted or added to the listed items For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

It is to be understood that each component, compound, substituent or parameter disclosed herein is to be interpreted as being disclosed for use alone or in combination with one or more of each and every other component, compound, substituent or parameter disclosed herein.

It is further understood that each range disclosed herein is to be interpreted as a disclosure of each specific value within the disclosed range that has the same number of significant digits. Thus, for example, a range from 1 to 4 is to be interpreted as an express disclosure of the values 1, 2, 3 and 4 as well as any range of such values.

It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range. That is, it is also further understood that any range between the endpoint values within the broad range is also discussed herein. Thus, a range from 1 to 4 also means a range from 1 to 3, 1 to 2, 2 to 4, 2 to 3, and so forth.

Furthermore, specific amounts/values of a component, compound, substituent or parameter disclosed in the description or an example is to be interpreted as a disclosure of either a lower or an upper limit of a range and thus can be combined with any other lower or upper limit of a range or specific amount/value for the same component, compound, substituent or parameter disclosed elsewhere in the application to form a range for that component, compound, substituent or parameter.

While particular embodiments have been described, alternatives, modifications, variations, improvements, and substantial equivalents that are or can be presently unforeseen can arise to applicants or others skilled in the art. Accordingly, the appended claims as filed and as they can be amended are intended to embrace all such alternatives, modifications variations, improvements, and substantial equivalents.

What is claimed is:

1. A fuel composition comprising a major amount of a fuel and a minor amount of a fuel additive including a quaternary ammonium salt including (i) a cation having a quaternary ammonium group and (ii) a N-substituted amino ketoacetate anion.

2. The fuel composition of claim 1, wherein the N-substituted amino ketoacetate anion has the structure of Formula I:

(Formula I)

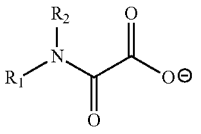

wherein $R_1$ is hydrogen, or selected from an alkyl group, an alkenyl group, an alkyl-ether group, an aryl-alkyl group, an alkyl-aryl group, an alkyl-aryl-ether group, an alkyl-polyether-alkyl group, or an aryl-polyether-alkyl group; and $R_2$ is hydrogen, or selected from an alkyl group, an alkenyl group, an alkyl-ether group, an aryl-alkyl group, an alkyl-aryl group, an alkyl-aryl-ether group, an alkyl-polyether-alkyl group, or an aryl-polyether-alkyl group.

3. The fuel composition of claim 1, wherein the N-substituted amino ketoacetate anion is derived from dialkyl oxalate or a monoalkyl oxalate anion reacted with an amine or polyamine having a primary or secondary amine.

4. The fuel composition of claim 1, wherein the cation having the quaternary ammonium group is derived from a polycarboxylic acid or anhydride reacted with an amine compound to form an intermediate reaction product including a quaternizable hydrocarbyl-substituted polycarboxylic acid or anhydride compound, wherein the amine compound includes at least one oxygen or nitrogen group capable of reacting with the polycarboxylic acid or anhydride and at least one quaternizable ammonium group; and wherein the intermediate reaction product is further reacted with a quaternizing agent that converts the at least one quaternizable amino group to a quaternary ammonium group to form the quaternary ammonium cation.

5. The fuel composition of claim 4, wherein the amine compound has the structure of Formula VIII:

$$(R_{15})(H)N—(CH_2)_a—X_m—(CH_2)_b—X_n—(CH_2)_c—N(R_{16})(R_{17}) \quad \text{(Formula VIII)}$$

wherein each X is a bivalent moiety selected from —O—, —N(R)—, —C(O)—, —C(O)O—, or —C(O)N(R)—;

$R_{15}$ is hydrogen or a hydrocarbyl group;

$R_{16}$ and $R_{17}$ are, independently, a hydrocarbyl group;

each R if present is, independently, a hydrogen atom or a group selected from $C_{1-6}$ aliphatic, phenyl, or alkylphenyl;

m and n are, independently, integers of 0 or 1; and a, b, and c are each, independently, an integer of 1 to 10.

6. The fuel composition of claim 4, wherein the amine compound has the structure of Formula IX $$R_{18}[OCH_2CHR]_n[OCHRCH_2]_mNR_{19}R_{19} \quad \text{(Formula IX)}$$

wherein each R if present is, independently, a hydrogen atom or a group selected from $C_{1-6}$ aliphatic, phenyl, or alkylphenyl;

$R_{18}$ is a hydrocarbyl group, n is an integer of 1 to 20, m is an integer of 1 to 20, and each $R_{19}$ is, independently, hydrogen or a hydrocarbyl group.

* * * * *